United States Patent
Hartmann et al.

(10) Patent No.: US 7,026,490 B2
(45) Date of Patent: Apr. 11, 2006

(54) AMORPHOUS ORGANIC 1,3,2-DIOXABORINE LUMINOPHORES, METHOD FOR THE PRODUCTION AND USE THEREOF

(75) Inventors: Horst Hartmann, Merseburg (DE); Arvid Hunze, Erlangen (DE); Andreas Kanitz, Höchstadt (DE); Wolfgang Rogler, Möhrendorf (DE); Dirk Rohde, Leipzig (DE)

(73) Assignee: Osram Opto Semiconductors GmbH, Regensburg (DE)

( * ) Notice: Subject to any disclaimer, the term of this patent is extended or adjusted under 35 U.S.C. 154(b) by 136 days.

(21) Appl. No.: 10/467,662

(22) PCT Filed: Feb. 7, 2002

(86) PCT No.: PCT/DE02/00457

§ 371 (c)(1),
(2), (4) Date: Aug. 11, 2003

(87) PCT Pub. No.: WO02/064600

PCT Pub. Date: Aug. 22, 2002

(65) Prior Publication Data

US 2004/0065867 A1 Apr. 8, 2004

(30) Foreign Application Priority Data

Feb. 9, 2001 (DE) .......................... 101 05 916

(51) Int. Cl.
- C07D 327/00 (2006.01)
- C09K 11/08 (2006.01)
- H01J 1/62 (2006.01)
- G03C 5/18 (2006.01)
- C07F 5/02 (2006.01)

(52) U.S. Cl. .................... 549/4; 252/301.4 R; 313/486; 428/690; 430/483

(58) Field of Classification Search .................... 549/4; 252/301.4 R; 313/486; 428/690; 430/483
See application file for complete search history.

(56) References Cited

U.S. PATENT DOCUMENTS

| | | | | | |
|---|---|---|---|---|---|
| 4,751,017 | A | * | 6/1988 | Wachtler et al. | 252/299.61 |
| 5,248,782 | A | * | 9/1993 | Haugland et al. | 548/110 |
| 5,827,863 | A | * | 10/1998 | Almansa et al. | 514/341 |
| 6,031,127 | A | * | 2/2000 | Yamamoto et al. | 562/443 |
| RE37,133 | E | * | 4/2001 | Maynard | 556/7 |
| 6,461,538 | B1 | * | 10/2002 | Taguchi | 252/301.17 |
| 6,559,310 | B1 | * | 5/2003 | Marcuccio et al. | 546/13 |
| 6,573,650 | B1 | * | 6/2003 | Aoki et al. | 313/503 |
| 6,596,196 | B1 | * | 7/2003 | Huguenin et al. | 252/301.4 R |
| 6,650,047 | B1 | * | 11/2003 | Aoki et al. | 313/506 |
| 6,673,928 | B1 | * | 1/2004 | Taguchi | 546/13 |
| 6,800,380 | B1 | * | 10/2004 | Kim et al. | 428/690 |
| 6,841,635 | B1 | * | 1/2005 | Kendall et al. | 526/195 |

FOREIGN PATENT DOCUMENTS

| | | |
|---|---|---|
| DE | 195 32 828 A1 | 3/1996 |
| DE | 100 02 424 A1 | 7/2001 |
| DE | 100 38 436 A1 | 3/2002 |
| WO | 01/53287 A2 | 7/2001 |
| WO | 02/12212 A1 | 2/2002 |

OTHER PUBLICATIONS

Database WPI, Section Ch, Week 199415, Derwent Publications Ltd., London, GB;, AN 1994–125119, XP002200050 & SU 1 148 291 A (Shershukov V M), Dec. 30, 1993 abstract.

* cited by examiner

Primary Examiner—Deborah C. Lambkin
(74) Attorney, Agent, or Firm—Young & Thompson

(57) ABSTRACT

The invention relates to luminophores having semiconducting properties and to the production and use thereof in organic luminous diodes (OLEDS) and organic solar cells. The novel materials are easy to prepare and exhibit excellent current density and efficiency when used in organic luminous diodes.

9 Claims, 2 Drawing Sheets a) Current density b) Efficiency

AMORPHOUS ORGANIC 1,3,2-DIOXABORINE LUMINOPHORES, METHOD FOR THE PRODUCTION AND USE THEREOF

CROSS REFERENCE TO RELATED APPLICATIONS

This is the 35 USC 371 National Stage of International Application PCT/DE02/00457 filed on Feb. 7, 2002, which designated the United States of America.

1. Field of the Invention

The invention refers to luminophores with semiconductor properties as well as their production and use in organic light emitting diodes (OLEDs) and organic solar cells.

2. Background of the Invention

Applications DE 10002423 and DE 10002424 (all previously unpublished) present new organic semiconductor materials that as solid bodies have a high fluorescence and form vitreous phases.

The new semiconductor materials are suitable for covering the spectral range emitting long-wave (orange to red) and belong to the "small molecules", although they can also be processed using spin coating. The materials are suitable both for the construction of organic light-emitting diodes (OLEDs) and also for constructing organic photovoltaic elements and can also be used to construct other organic electronic elements, with it being possible to use these materials in whole transport layers, electron transport layers and emitter layers.

The materials are easy to prepare in high yields and are derived from 2-N, N-Di (het) arylamino-thiophene and/or -thiazo derivates.

There is a continuing need for new organic semiconducting and/or emitting materials for a variety of applications in organic components and light-emitting diodes.

SUMMARY OF THE INVENTION

The object of the invention is to provide new organic, amorphous, long-wave electroluminescent compounds that can be used in organic light-emitting diodes and/or organic electronic components, that are easy to prepare and can be easily processed using mass production methods.

The object of the invention is 1,3,2-Dioxaborine luminophores of types XI, XII and XIII (reaction schematic C) XIV and/or XV (reaction schematic D) whereby the following applies:

$R^1$, $R^2$, $R^3$, $R^4$ and $R^9$ are, independent of each other, in each case a monofunctional (het) aryl system, i.e. a conjugated carboxylic and heterocyclic ring system that can also consist of linear or angular fused or combined ring types that are the same or different, whereby the peripheral hydrogen atoms may also be substituted by alkyl, alkoxy, phenoxy, dialkylamino or diphenylamino groups (alkyl= $C_1$ to $C_6$);

furthermore, $R^1$ and $R^2$ in compound type XV can also be branched or unbranched alkyl groupings ($C_1$–$C_6$) or, together with the bonded N atom, can jointly form a pyrrolidine, piperidine or morpholine ring;

$R^3$ and $R^4$ can also be H independent of each other;

$R^8$ can be a chemical compound or a corresponding bi-functional (het) arylene system, i.e. a conjugated carboxylic or heterocyclic ring system that can also consist of linear or angular fused or combined ring types that are the same or different, whereby the peripheral hydrogen atoms can also be substituted by alkyl, alkoxy, phenoxy, dialkylamino or diphenylamino groups (alkyl=$C_1$ to $C_6$).

Furthermore, it is the object of the invention to provide a method for the production of compound of types XI, XII, XIII, XIV and XV.

Finally it is the object of the invention to use the compounds of type XI, XII, XIII, XIV and XV in organic light-emitting diodes, organic solar cells, photo-refractive components and/or other electronic components with organic functional layers.

DETAILED DESCRIPTION OF THE INVENTION

Figure 1:
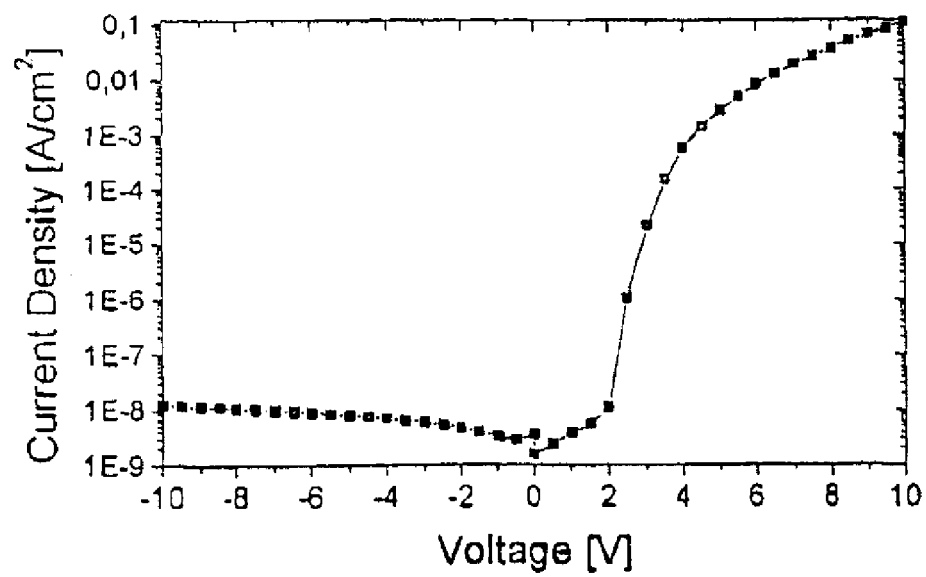
FIG. 1 shows the current density and efficiency of the characteristics of an OLED from Example 15.
Figure 1:
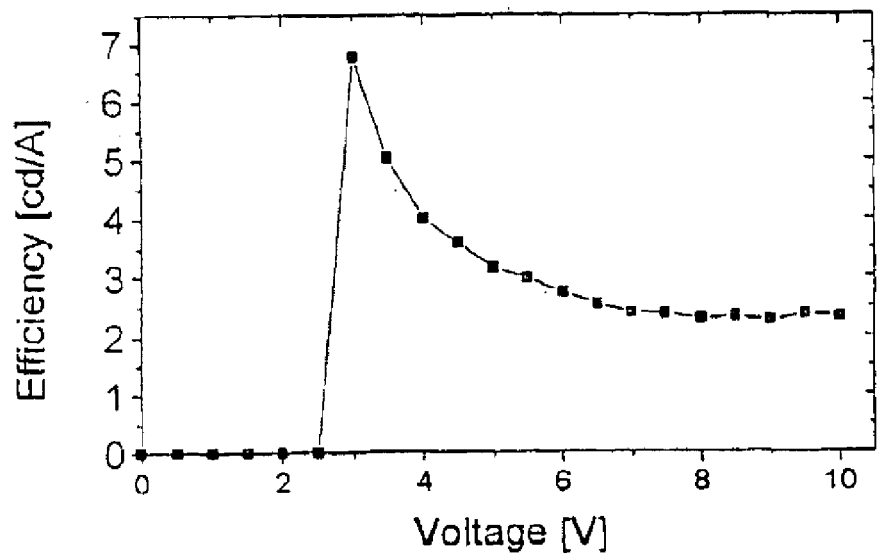
Figure 2:
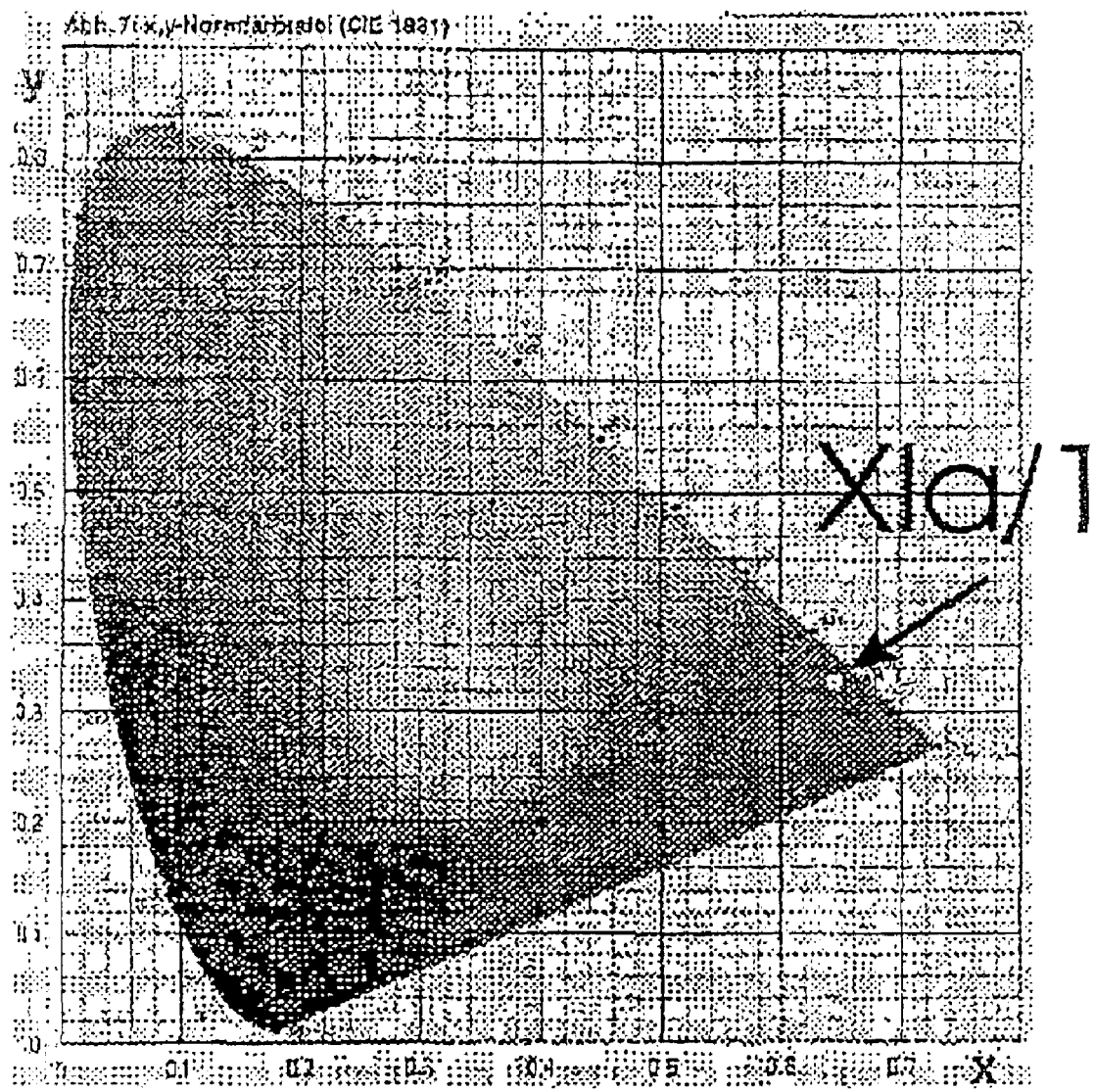
FIG. 2 shows the CIE data of an OLED from Example 15.

The new compounds in accordance with the invention are easy to prepare and are all derived from a modular system (see reaction schematics A-D) of N, N-disubstituted carboxylic acid amides II or N, N-disubstituted thiocarboxylic acid amides IV. They can be easily processed as part of a mass production process.

For formation of the initial synthons and dioxaborine precursors, the following applies.

$R^5$ and $R^6$ are H, $C_1$ to $C_{10}$ alkyl or phenyl independent of each other or jointly form a $C_4$ to $C_6$ alkylene grouping or a —$CH_2$—$CH_2$—O—$CH_2$—$CH_2$— grouping; $R^7$ is a branched or unbranched alkyl residue;

X is a halogen, preferably Cl, Br or I;

$A^-$ is the anion of the Vilsmeier reagent, preferably also $ClO_4^-$.

$R^{10}$ has the significance of $R^1$, but preferably the significance of structure type VIII, whereby $R^1$ and $R^2$ in compound type VIII can also mean branched or unbranched alkyl groupings ($C_1$–$C_6$) or, together with the combined N atom, form a pyrrolidine, piperidine or morpholine ring.

Reaction Schematic
A: Formation of initial synthons.

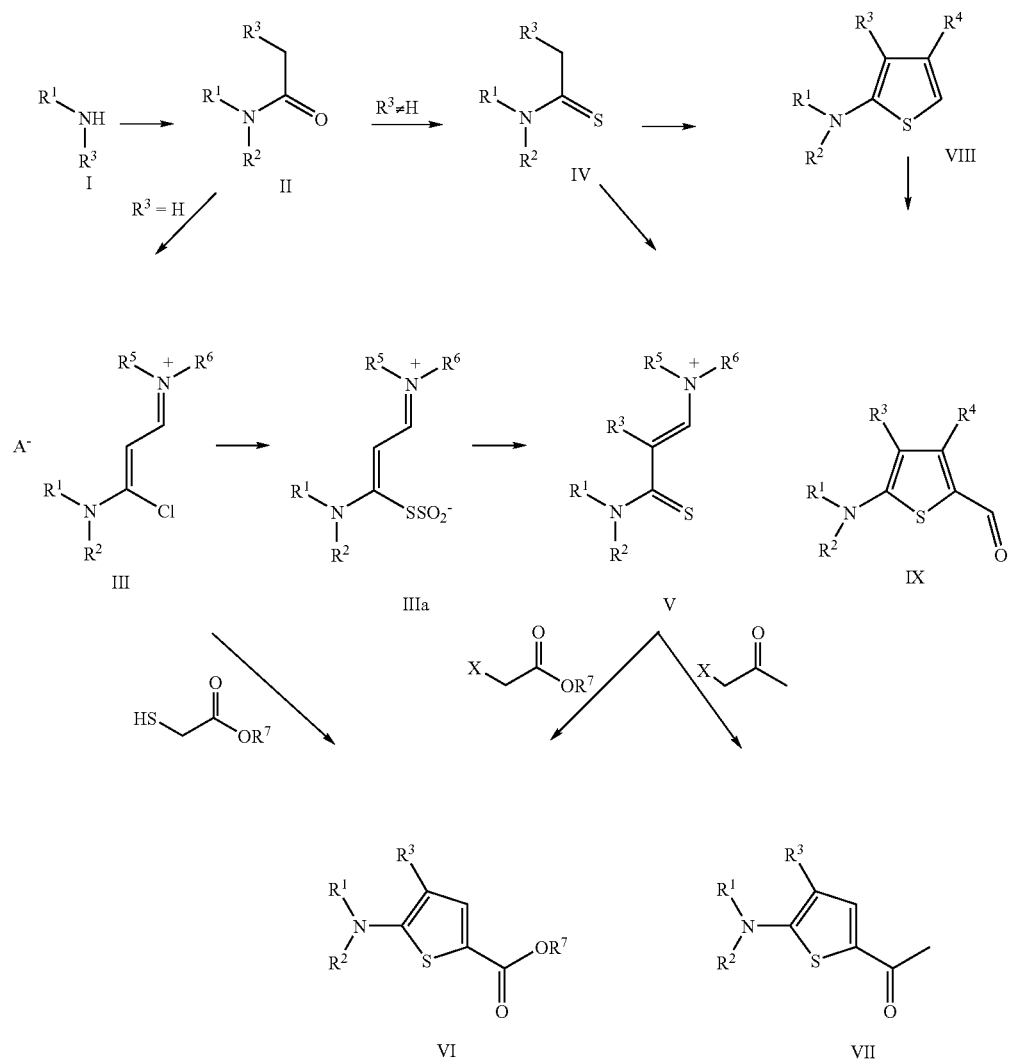

Starting from the carboxylic acid amides II, the initial synthons are the vinylogous thiocarboxylic acid amides V, the 2-N, N-disubstituted amino thiophene-5-yl-carboxylic acid ester VI, the 2-N, N-disubstituted amino thiene-5-yl-acetophenones VII and the 2-N, N-disubstituted aminio-5-formnyl-thiophenes IX (reaction schematic A) are easy to prepare in high yields for the representation of the electroluminance luminophores.

The recovery of the vinylogous thiocarboxylic acid amides V in this case is achieved by two different synthesis routes. For the representation of the 3-substituted vinylogous thiocarboxylic acid amides V, the corresponding carboxylic acid amides II are converted to the associated thiocarboxylic acid amides IV by means of the Lawessons reagent, in order in the next reaction step to obtain the synthon V by an amino formylation according to Liebscher using ethyl orthoformate and an amine with a boiling point above 100° C. The 3-unsubstituted vinylogous thiocarboxylic acid amides V are on the other hand produced from the carboxylic acid amides II by an Arnold reaction that generates chloropropene iminium salt III, from which the synthons V are obtained via the coloured salts stage by reaction using a thiosulphate and then a sulphide extrusion.

From the thiocarboxylic acid amides IV, that are converted by an analogue Hantz reaction to the corresponding 2-N, N-disubstituted amino thiophenes VIII, 2-N, N-disubstituted amino-5-formyl-thiophenes IX can be obtained by a Vilsmeier reaction.

From the vinylogous thiocarboxylic acid amides V, the synthons VI can be obtained by conversion using 2-halogen acetic acid esters in analogue Hantz reactions, and the synthons VII obtained by conversion using 2-halogen acetone. The 3-unsubstituted synthons VI can also be formed directly from the Arnold products III by thioacetic acid ester due to S-alkylation and cyclization as well as their stabilisation by condensation to aromatics.

B: Representation of the 1,3,2-dioxaborine precursors.

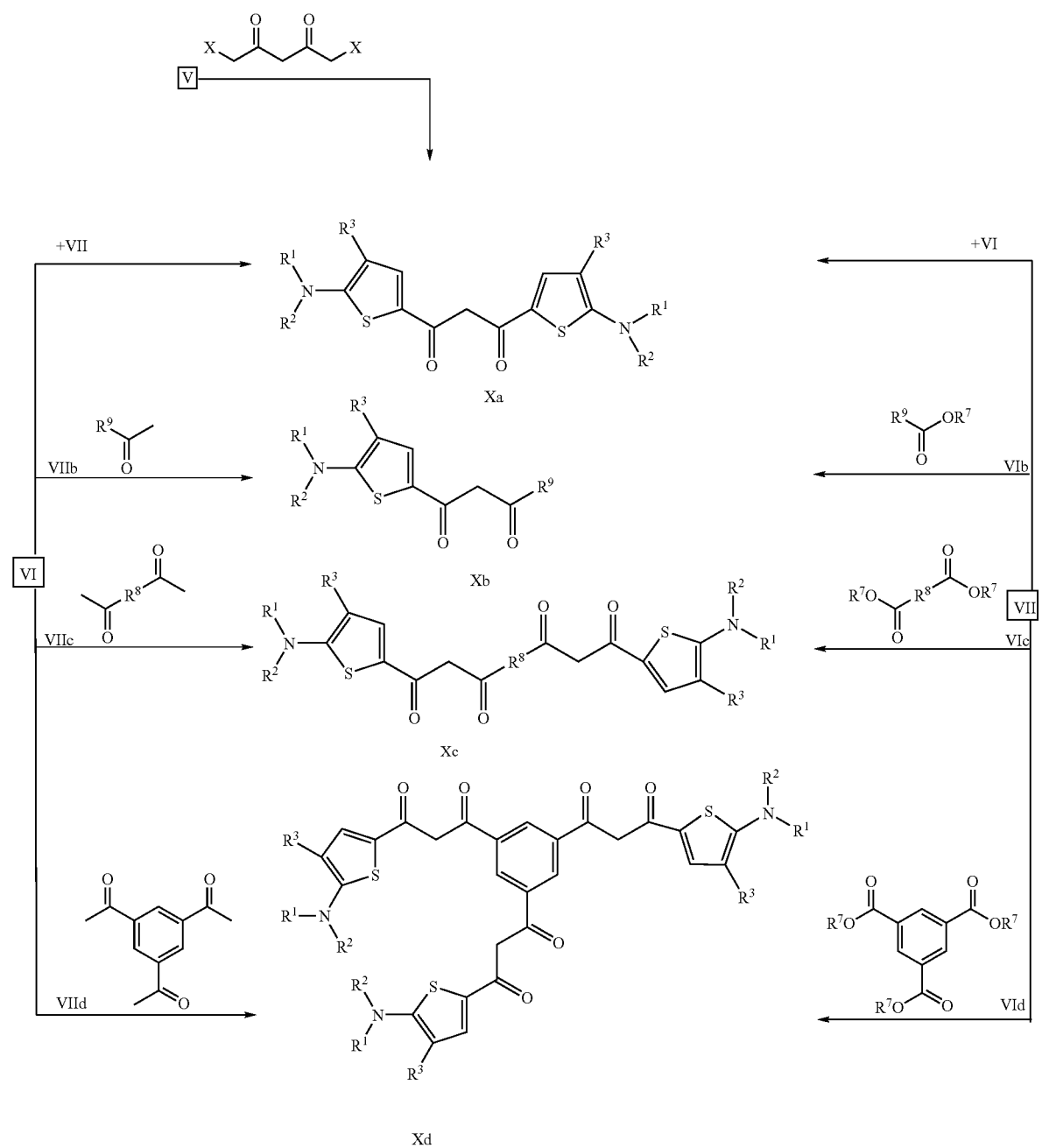

The representation of the 1,3,2-dioxaborine precursors, the 1,3-diketone X (reaction schematic B) takes place from synthons V, VI and VII.

The substituted 1,3-dithienyl propane-1,3-diones Xa are obtained by means of a bi-functional analogue Hantz reaction during the conversion using 1,5-dihalogen pentane-2,4-diones.

A further simple method of synthesising the dioxaborine precursors Xa is in a Claisen condensation from type VI thienyl carboxylic acid esters using type VII thienyl acetophenons in the presence of a strong base in a non-polar solvent.

In a similar way, corresponding unsymmetric 1,3,2-dioxaborine precursors of type Xb are created by converting the type VI thienyl carboxylic acid esters with any acetophenons VIIb or vice versa by converting the thienyl acetophenons VII with any (het) aryl carboxylic acid esters VIb. To obtain bi- and tri-1,3,2-dioxaborine precursors Xc or Xd, corresponding diacetyl derivate VIIc or triacetyl derivate VIId are converted with the thienyl carboxylic esters of type VI or the corresponding di- or tricarboxylic ester VIc or VId with the thienyl acetophenons of type VII.

C: Formation of dioxaborine:
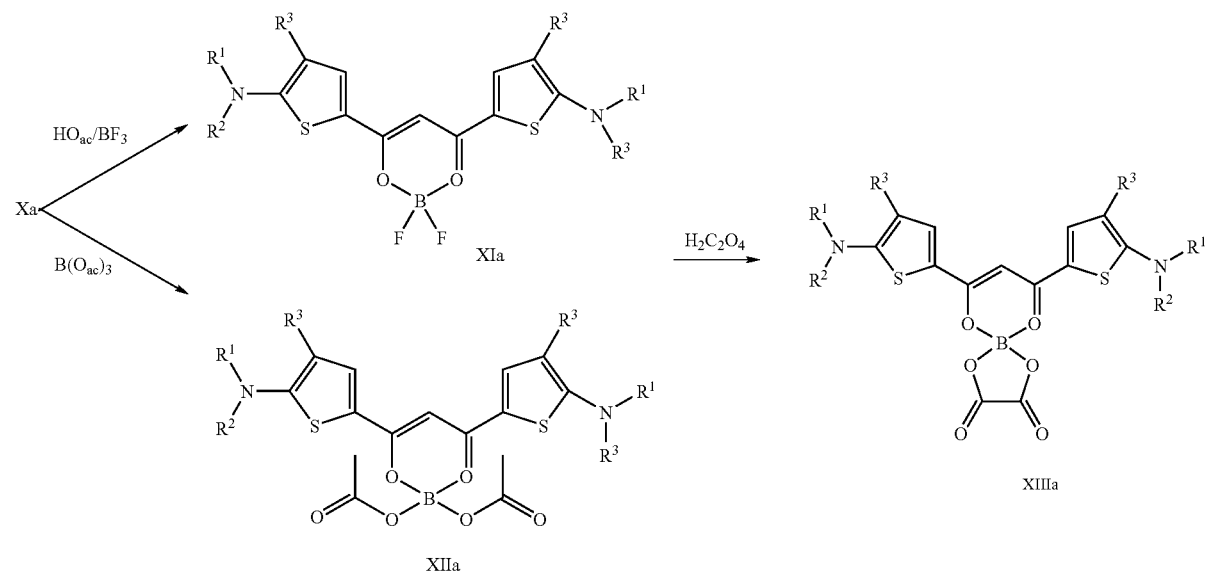
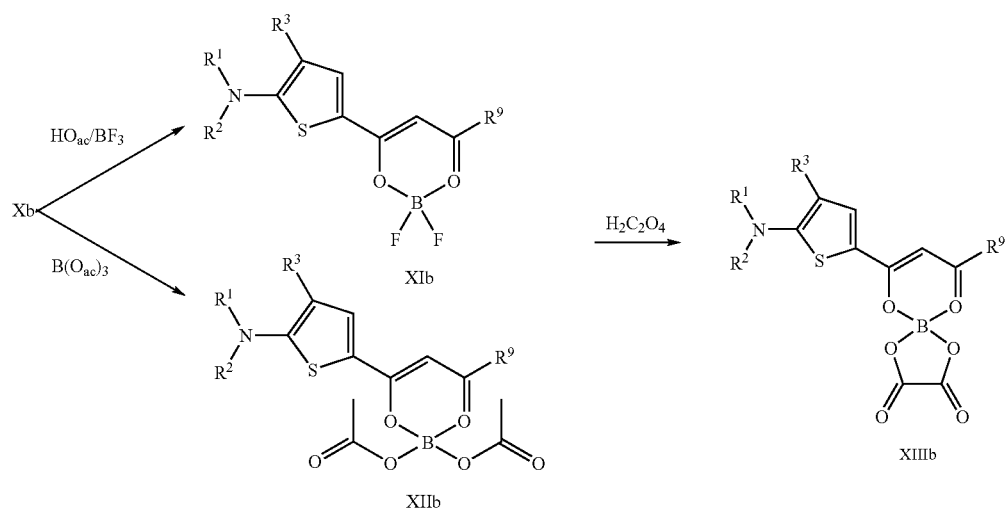
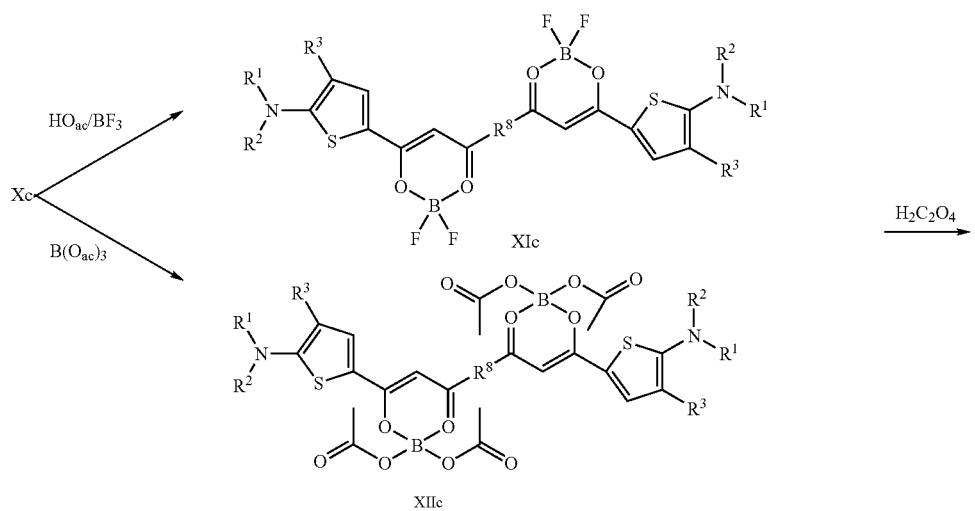

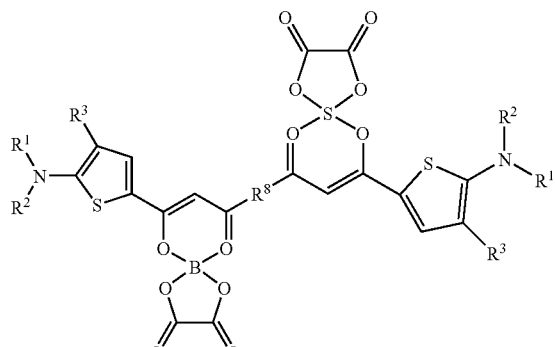
XIIIc
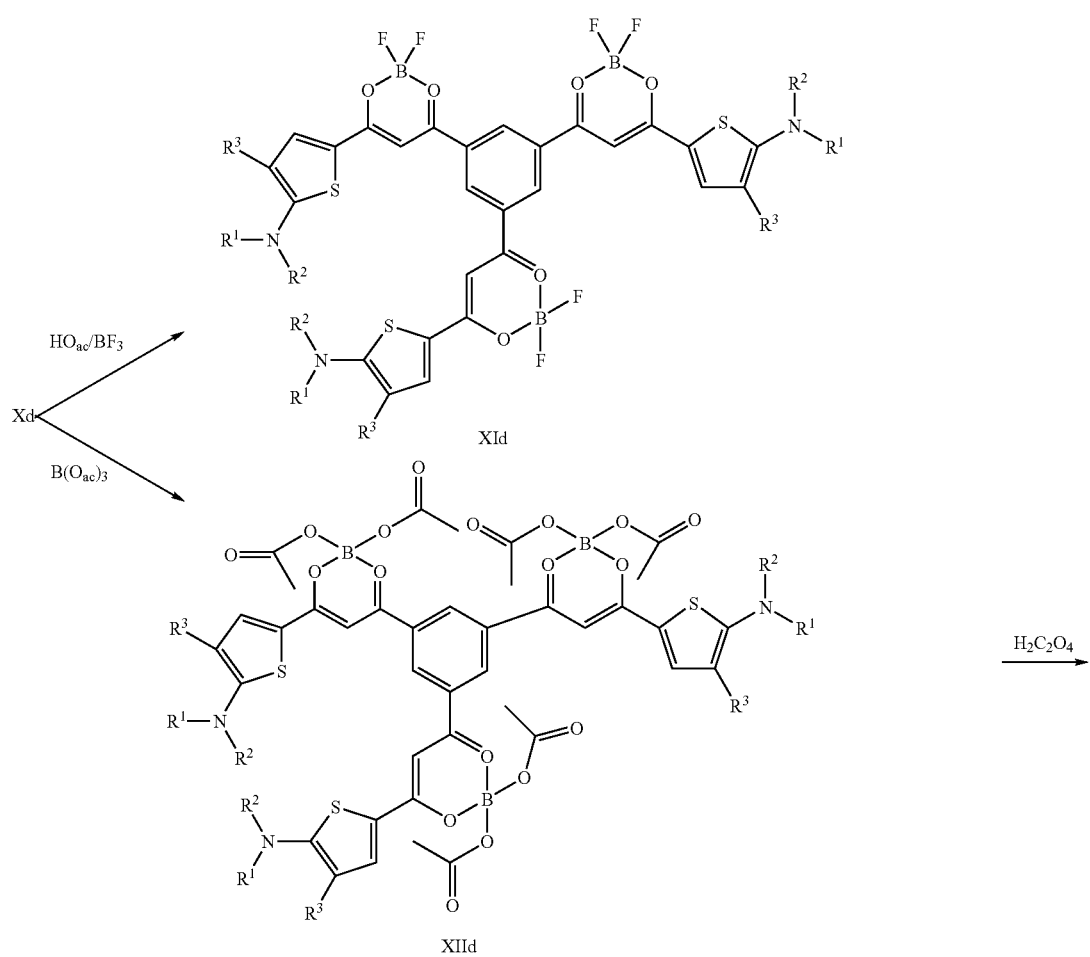

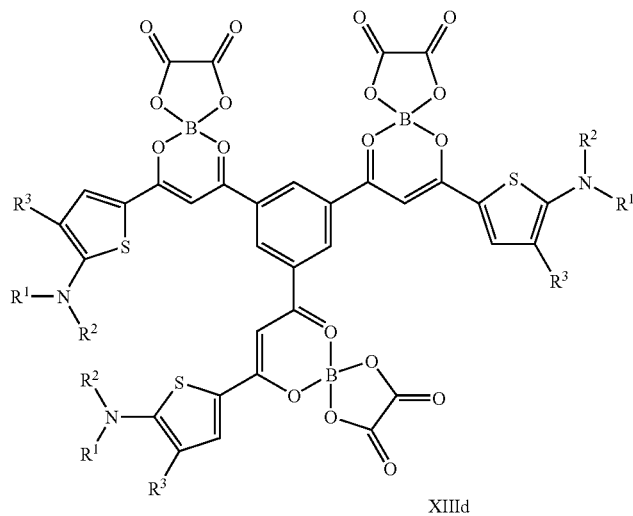

XIIId

The particularly simple conversion of the 1,3-diketo derivate X to the 1,3,2-dioxaborine luminophores XI and XII and also the ligand exchange for forming the 1,3,2-dioxaborin luminophores XIII is shown in reaction schematic C. For this purpose, the 1,3-diketo derivate is heated for a short time up to reflux in acetic anhydride with a boric acid derivate (acetic acid-boron trifluoride complex or boron triacetate), with the luminophores XI and XII according to the invention occurring during cooling.

The boron ligands in the complex XII can also be alkyl or aryloxyl ligands, whereby the alkyl groupings, branched or unbranched, can contain 1 to 18 C atoms. The formation of the corresponding boron ester takes place in situ by thermal dehydration of the corresponding carboxylic acids in the presence of boric acid.

Furthermore, in dichlorethane a ligand exchange can be achieved with the 2,2-diacetyl- 1,3,2-dioxaborines XII, that in the presence of oxalic acid contain the 2,2-oxalato-1,3,2-dioxaborines XIII, that are still emitting in the long-wave and are stable.

Other dicarboxylic acids can, of course, be used for this ligand exchange, preferably with oxalic acid, malonic acid, alkyl malonic acid or dialkyl malonic acid.

D: Formation of (het)-arylstyryl-substituted dioxaborines:

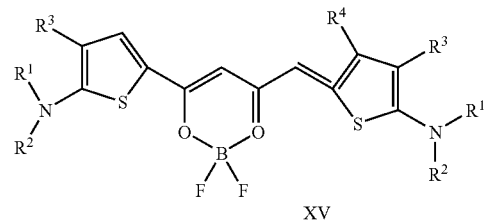

XV

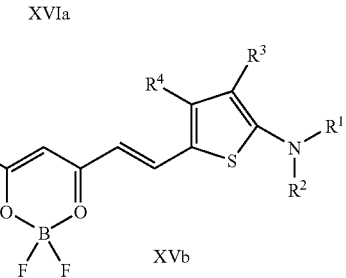

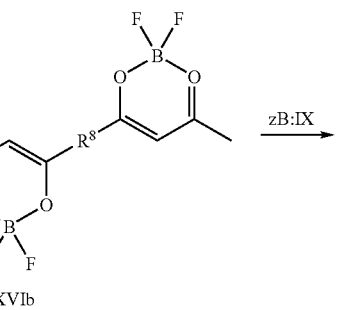

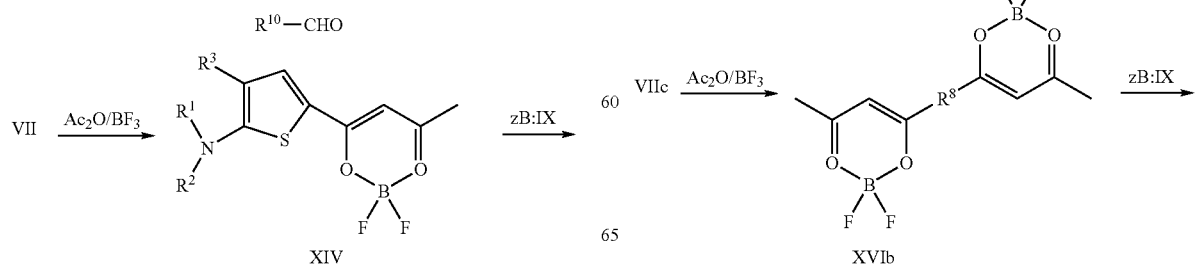

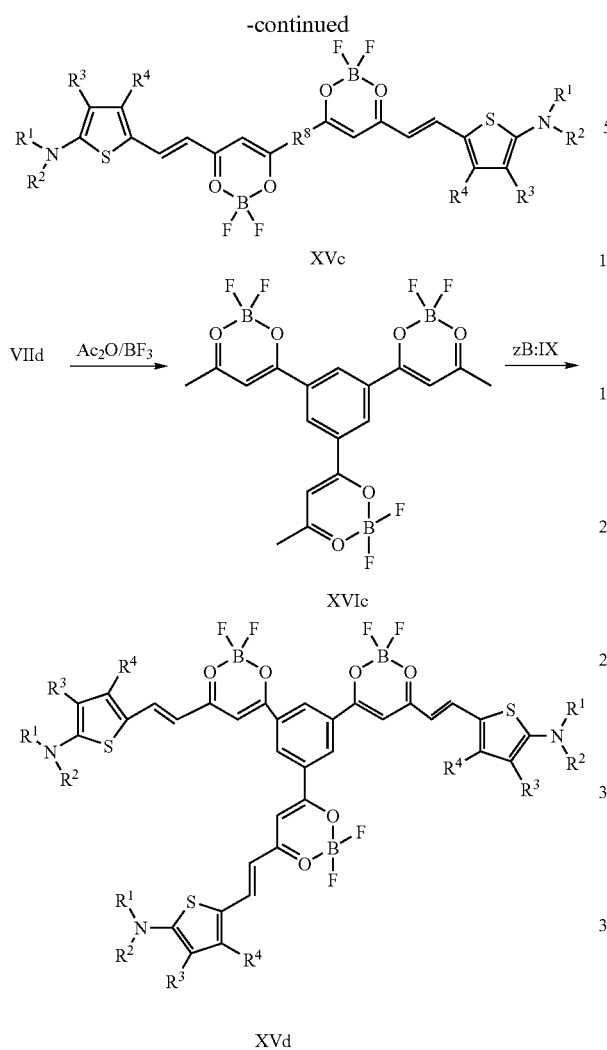

XVc

XVIc

XVd

In reaction schematic D, a further method for representing 2,2-difluoro-1,3,2,-dixaborines is used, to show vinylogous 1,3,2-dioxaborine luminophores XV. For this purpose, the known acylation reaction of acetyl compound VII, produced by boron trifluoride in acetic anhydride, is used to form the methylene-active 4-methyl-6-(het)aryl-2,2-difluoro-1,3,2-dioxaborines XIV and XVI, that by means of any (het)aryl aldehydes, but preferably with type IX compounds, are converted into previously unknown, long-wave emitting luminophores XV with amorphous properties.

The amorphizity of the new chromophores XI, XII, XIII, XIV and XV has a tendency to increase in line with the degree of aryl substitution in the hetero aromatic parent substances. They can be processed by a coating method using solutions and by evaporation, whereby these emitter materials can be used doped in an electron transport material or, in the case of peraryl substitution, also combined as an emitter and electron transport material.

Examples of embodiments:

Examples 1 to 14 explains the general synthesis instruction of the substance classes using individual examples. The construction of an organic light emitting-diode (OLED) and its physical characteristics are shown in example 15.

EXAMPLE 1

Synthesis of Carboxylic Acid Amides II

In a 2 l three-neck flask with a reflux condenser, magnetic stirrer, dropping funnel and inert gas flow, 1 mol of a secondary amin I is dissolved in each case in 600 ml of dioxane. The carboxylic acid halogenide required in each case is then added by drops in an equivalent amount. The reaction mixture is then heated under reflux until the complete amount of the hydrohalogenide produced by the reaction has been removed from the inert gas flow. The end of the reaction can additionally be detected by monitoring using thin-layer chromatography. The reaction solution is then cooled down and stirred into at least twice the amount of water. In most cases this causes an oil to separate which solidifies after a few hours. The aqueous phase is separated and the raw product recrystallised from ethanol. The yield in each case is at least 90%.

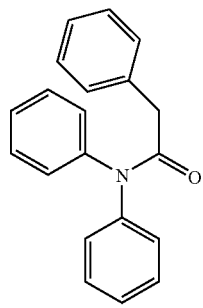

In this way, for example, 2-phenyl acetic acid diphenyl amide (mp: 71–72° C.) is produced from diphenylamine and 2-phenyl acetyl chloride.

EXAMPLE 2

Synthesis of Thiocarboxylic Acid Amides IV 0.5 mol of the particular carboxylic acid amide II and the equivalent amount of Lawesson reagent (produced from anisole and phosphorous pentasulphide) are suspended in a reflux apparatus with an inert gas throughflow in 750 ml of diglycolic diethyl ether and is then stirred at 100° C. for 6 hours. This causes a clear solution to form from which in some cases the reaction product crystallises out in the cold. To isolate the product completely, the reaction mixture is stirred into twice the amount of water, and the oleaginous phase which often forms can then be crystallised. The product is then separated from the aqueous phase and recrystallised from methanol. The yield in each case is at least 90%.

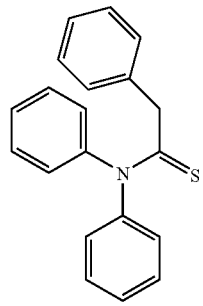

In this way, for example, 2-phenyl-thioacetic acid-diphenyl amide (mp: 142–144° C.) is produced from 2-phenyl acetic acid diphenyl amide and the Lawesson reagent.

EXAMPLE 3

Synthesis of Chloropropene Iminium Salts III 0.5 mol of the particular carboxylic acid amide II is suspended in 1.5 mol DMF in a 2 l beaker. 1.25 mol POCl₃ is added by drops to this suspension so that the temperature of the reaction mixture is between 50 and 60° C.; if necessary an ice bath is used for cooling. In the course of the reaction a complete solution is produced that is held at 60° C. for up to 30 minutes after the POCl₃ is added, and is then cooled. A mixture of 0.5 mol of 70% perchloric acid and methanol is then carefully added to the reaction solution to decompose the excess Vilsmeier reagent. The amount of methanol used should be approximately double the volume of the reaction solution. The chlorovinyl iminium salt formed by the conversion precipitates in the form of perchlorate during cooling. The yield in each case is at least 85%.

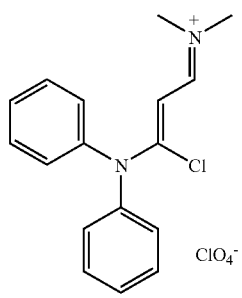

In this way, for example, 1-chloro-1-diphenyl amino propene-3-yl-dimethyl iminium perchlorate (mp: 178–180° C.) is produced from acetic acid diphenyl amide and POCl₃ in DMF.

EXAMPLE 4

Synthesis of Vinylogous Thiocarboxylic Acid Amide V a) from thiocarboxylic acid amides IV 0.2 mol of the particular thiocarboxylic acid amid IV, 0.8 mol triethyl orthoformate and 0.6 mol morpholine are heated in a flask, containing a magnetic stirrer, water separator and reflux condenser, at 130° C. until 0.6 mol ethanol has separated in the water separator. After cooling, the reaction solution is stirred into five times that amount of water and is then neutralised using glacial acetic acid. The product that has crystallised out is separated and recrystallised from methanol. The yield in each case is at least 90%.

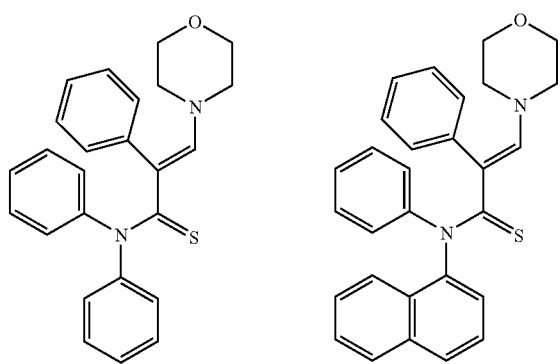

In this way, for example, 3-morpholino-2-phenyl-thioacrylic acid diphenyl amide (mp: 182° C.) is produced from 2-phenyl thioacetic acid diphenyl amide in the presence of triethyl orthoformate acid ester and morpholine and also 3-morpholino-2-phenyl-thioacrylic acid-N-phenyl-N-1-naphthylamide (mp: 185° C.) from 2-phenyl thioacetic acid-N-phenyl-N-1-naphthylamide in the present of triethyl orthoformate acid ester and morpholine.

b) from chloropropene iminium salts III 0.2 mol of the particular chlorovinyl iminium salt III and 0.2 mol sodium thiosulphate are suspended in 500 ml of methanol in a reflux apparatus, and then heated under reflux to form a clear solution. By adding 0.4 mol of aniline, the coloured salt IIIb thus produced is converted to the anil of the vinylogous thiocarboxylic acid amide V, that already begins to crystallise in the heat and has completely precipitated after cooling. After adding 100 ml of water, the product is drawn off. The yield in each case is at least 80%.

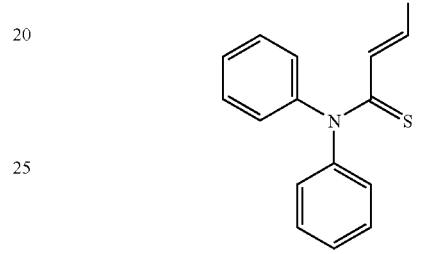

In this way, for example, 3-dimethyl amino thioacrylic acid diphenyl amid (mp: 185–187° C.) is produced from 1-chloro-1-diphenyl amino propene-3-yl-dimethyl iminium perchlorate.

EXAMPLE 5

Synthesis of Thienylcarboxylic Acid Ester VI a) from vinylogous thiocarboxylic acid amides V 0.1 mol of the particular vinylogous thiocarboxylic acid amide V with the equivalent amount of α-haloacetic acid ester in 300 ml of ethanol is heated at reflux for the 30 minutes whilst stirring in a flask with a reflux condenser. This produces a complete solution. Then, 0.1 mol of triethyl amin is then added and allowed to cool for a further 5 minutes, which causes triethyl ammonium halide to precipitate and the product also precipitates. The product is treated using 100 ml of water and the crystallised product is drawn off, dried and then recrystallised from ethanol or ethanol/water. The yield amounts to at least 80% d.T.

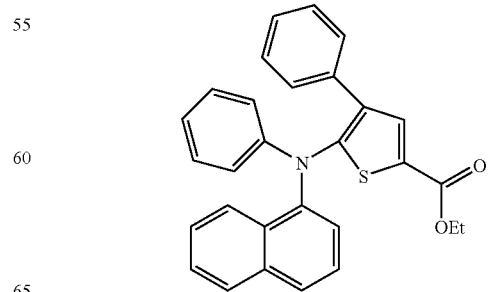

In this way, for example, 2-(N-1-naphthyl-N-phenyl-amino)-3-phenylthien-5-yl-carboxylic acid ethyl ester VI/1 mp: 57° C. is produced.

b) from chloropropene iminium salts III 0.1 mol of the particular chloropropene iminium salts III with the equivalent amount of mercaptoacetic acid ester in 150 ml of ethanol is heated at reflux for the 30 minutes whilst stirring in a flask containing a reflux condenser. This produces a complete solution. Then, 0.1 mol of triethyl amin is then added and allowed to cool for a further 5 minutes, which causes the triethyl ammonium halide to precipitates and the product also precipitates. The product is treated using 100 ml of water and the crystallised product is drawn off, dried and then recrystallised from ethanol or ethanol/water. The yield amounts to at least 80% d.T.

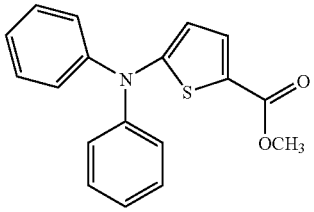

In this way, for example, 2-(N, N-diphenyl)-amino-thien-5-yl-carboxylic acid methyl ester VI/2 mp: 55° C. is produced.

EXAMPLE 6

Representation of the Acetyl Thiopenes VII 0.1 mol of the particular vinylogous thiocarboxylic acid amide V is heated with the equivalent amount of chloroacetone in 150 ml THF in a flask with a reflux condenser whilst stirring for 30 minutes heated to reflux. This produces a complete solution. 0.1 mol of triethylamine is then added and allowed to cool for a further 5 minutes, which cause the triethylammonium halide to precipitate. THF is removed from the reaction mixture at the rotary evaporator and then treated with 10 ml of glacial acetic acid and 100 ml of water. The product crystallises and is drawn off, dried and recrystallised from ethanol or ethanol/water. The yield is at least 70% d.T.

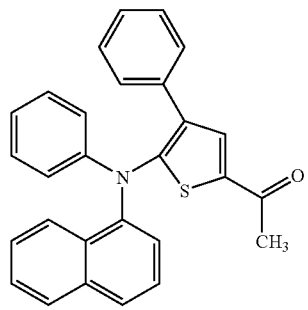

In this way, for example, 2-(N-1-naphthyl-N-phenyl)-amino-3-phenyl-5-acetylthiophene VII/1 mp: 135–137° C. is produced.

EXAMPLE 7

Synthesis of 2-aminothiophenes VIII 0.1 mol of the particular thiocarboxylic acid amide IV is heated with the equivalent amount of aromatic ω-haloacetyl compound in 200 ml DMF in a flask with a reflux condenser, stirring for 5 hours heated to 120° C. This produces a complete solution. It is then allowed to cool. The reaction mixture is added to 300 g of crushed ice while stirring causing the product to crystallise. It is then drawn off, dried and recrystallised from ethanol. The yield is at least 70% d.T.

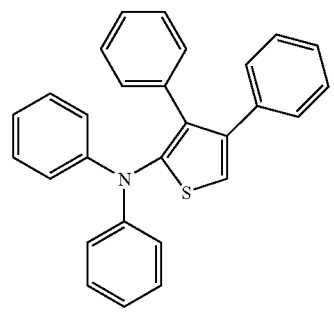

In this way, for example, 2-(N, N-diphenyl)-amino-3,4-diphenyl-thiophene VIII/1 mp: 105° C. is produced.

EXAMPLE 8

Synthesis of 2-amino-5-formylthiophenes IX 0.1 mol of the particular 2-aminothiophenes VIII in a beaker is digested using 50 ml DMF and cooled so that by adding 0.15 mol $POCl_3$ by drops the temperature does not exceed 20° C. This produces a complete solution that when all the additive has been added is again heated to 60° C. for 30 minutes. The reaction mixture is added to 300 g of crushed ice while stirring causing the product to crystallise. It is then drawn off, dried and recrystallised from ethanol. The yield is at least 60% d.T.

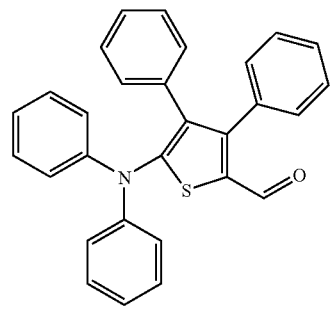

In this way, for example, 2-(N, N-diphenylamino)-3,4-diphenyl-5-formulthiophene IX/1 mp: 116° C. is produced.

EXAMPLE 9

Synthesis of dithienyl propane-1,3-diones Xa a) From vinylogous thiocarboxylic acid amides V A mixture consisting of a vinylogous thiocarboxylic acid amide V (0.002 mol) and 1,5-dichloro-pentane-2,4-dion (0.001 mol) in acetonitrile (50 ml) is briefly heated in the water bath and then treated with triethylamine (1 ml). The product produced during cooling by adding water (10 ml) is drawn off and air dried.

In this way, for example, the compound of type Xa is obtained:

1,3-bis-(2-diphenylamino-thien-5-yl)-propane-1,3-dion in a yield of 71% and a mp=302° C.;

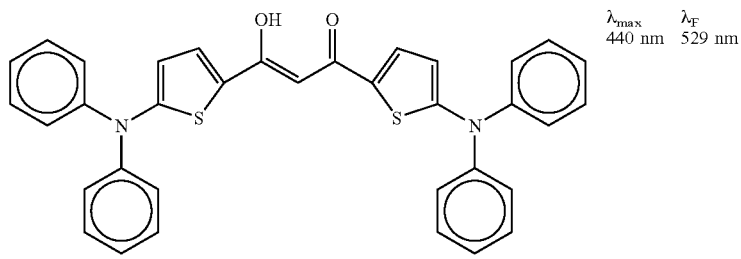

b) from thienylcarboxylic acid esters VI and acetyl thiophenes VII

A mixture consisting of thienylcarboxylic acid ester VI (0.1 mol) and acetylthiophene VII (0.1 mol) is added by drops while stirring to a suspension consisting of sodium hydride (0.12 mol) in toluene (250 ml). It is then heated for 10 hours with reflux and after cooling the reaction mixture is poured into aqueous acetic acid. The product produced is drawn off and recrystallised from glacial acetic acid or ethyl acetate.

In this way, for example, the same compound of the type Xa is obtained:

1,3-bis-(2-diphenyl aminothiene-5-yl)-propane-1,3-dion in a yield of 56% and mp of 302° C.

EXAMPLE 10

Synthesis of the 1,3-diketo derivates Xb–Xd a) from thienylcarboxylic acid esters VI and acetyl derivate VIIb–VIId.

A mixture of a thienylcarboxylic acid ester VI (0.1 mol) and an acetyl derivate VIIb (0.1 mol); VIIc (0.05 mol) and VIId (0.033 mol) is added by drops while stirring to a suspension of sodium hydride (0.12 mol) in toluene (250 ml). The mixture is then heated with reflux for 10 hours in the case of VIIb or 48 hours in the case of VIIc and VIId and after it has cooled down the reaction mixture is poured into an aqueous acetic acid. The resulting product is drawn off and recrystallised from glacial acetic acid or ethyl acetate.

In this way, for example, the following synthons Xb–Xd are produced.

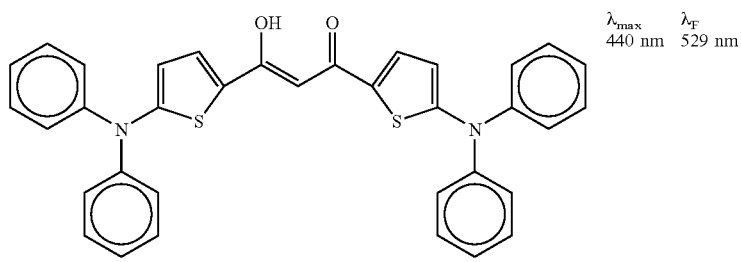

| | | λ_max | λ_F | mp | Yield |
|---|---|---|---|---|---|
| Xb/1 | | 441 nm | 528 nm | 132° C. | 32% |
| Xc/1 | | 452 nm | 544 nm | 220° C. | 15% |
| Xc/2 | | 443 nm | 547 nm | 226° C. | 34% |
| Xc/3 | | 361 nm | 449 nm | 156° C. | 32% |
| Xc/4 | | 377 nm | 487 nm | 195° C. | 28% |
| Xd/1 | | 447 nm | 544 nm | 262° C. | 38% | b) from acetyl thiophenes VII and an ester derivate VIb–VId

A mixture of acetyl thiophenes VII (0.2 mol) and an ester derivate VIb (0.2 mol); VIc (0.1 mol); VId (0.067 mol) is added by drops while stirring to a suspension of sodium hydride (0.24 mol) in toluene (350 ml). The mixture is then heated with reflux for 48 hours and after it has cooled down the reaction mixture is poured into an aqueous acetic acid. The resulting product is drawn off and recrystallised from glacial acetic acid or ethyl acetate.

In this way, for example, the compound Xc/1 (R$^1$, R$^2$=phenyl, R$^3$=H, R$^8$=chemical bonds) is produced with a yield of 59%; mp: 205–207° C.

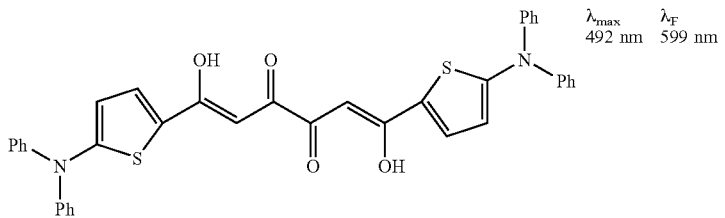

Xc/1 — λmax 492 nm, λF 599 nm

EXAMPLE 11

Synthesis of 1,3,2-dioxaborines XI and XII

A mixture of a 1,3-diketo derivate X (0.001 mol) in acetic anhydride (100 ml) is treated with a boric acid derivate (0.002 mol) acetic acid-boron trifluoride-complex or boron triacetate for XIa, XIIa, XIb and XIIb; (0.004 mol) acetic acid-boron trifluoride-complex or boron triacetate for XIc and XIIc and (0.006 mol) acetic acid-boron trifluoride-complex or boron triacetate for XId and XIId and then heated for 30 minutes with reflux. After cooling down, the product produced is drawn off and cleaned by recrystallising from glacial acetic acid.

In this way, for example, the following 1,3,2-dioxaborines XI and XII are produced.

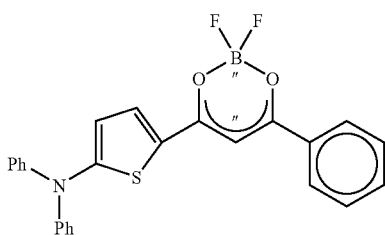

XIb/1 — λmax 501 nm, λF 606 nm, mp Tg 258° C. 99° C., Yield 40%

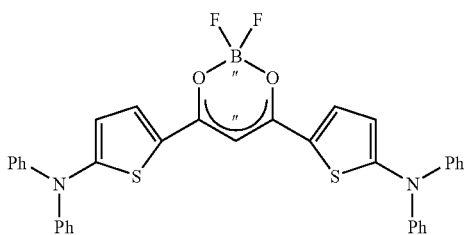

XIa/1 — λmax 566 nm, λF 622 nm, mp Tg 302° C. 94° C., Yield 37%

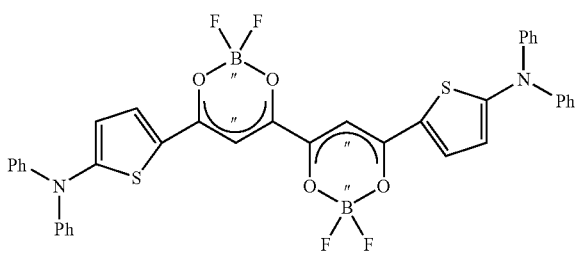

XIc/1 — λmax 629 nm, λF 725 nm, mp >360° C., Yield 45%

| | | | | | |
|---|---|---|---|---|---|
| XIc/2 | 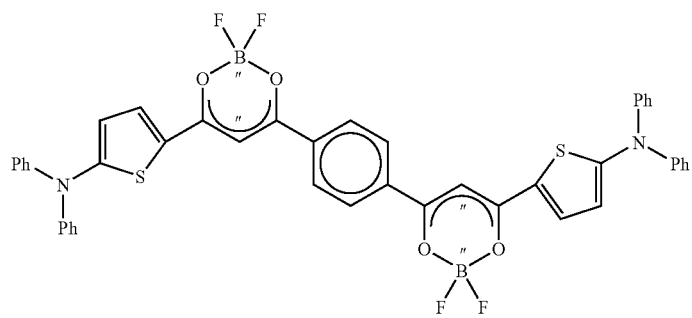 | λ_max 554 nm | λ_F 654 nm | mp >360° C. | Yield 30% |
| XIc/3 | 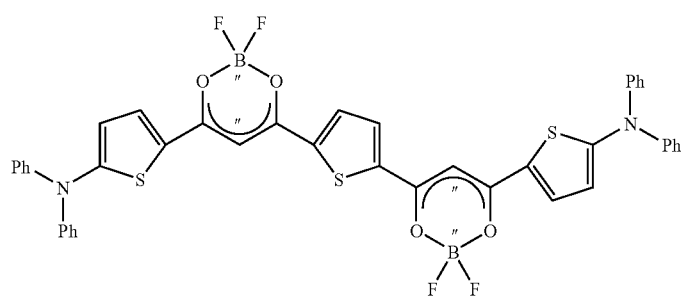 | λ_max 538 nm | λ_F 627 nm | mp 262° C. | Yield 34% |
| XIc/4 | 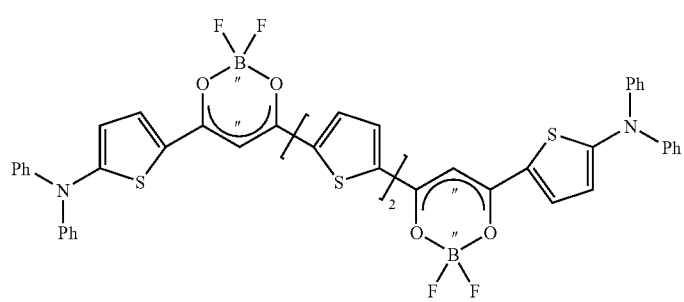 | λ_max 561 nm | λ_F 661 nm | mp 261° C. | Yield 38% |
| XIc/5 | 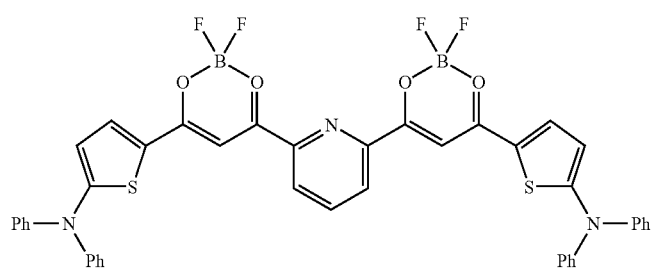 | λ_max 505 nm[c)] | λ_F 610 nm[c)] | mp >360° C. | Yield 41% |

-continued

| | | | | | |
|---|---|---|---|---|---|
| XId/1 | [structure] | $\lambda_{max}$ 530 nm[a)] | $\lambda_F$ 639 nm[a)] | mp >360° C. | Yield 33% |
| XIIa/1 | [structure] | $\lambda_{max}$ 566 nm | $\lambda_F$ 613 nm | mp Tg 234 47 | Yield 65% |

EXAMPLE 12

Synthesis of the 1,3,2-dioxaborines XIII

A mixture of 2,2-diacetyl-1,3,2-dioxaborine XII (0.001 mol) in dichlorethane (100 ml) is treated using oxalic acid (0.002 mol) for XIIIa and XIIIb; (0.004 mol) for XIIIc and (0.006 mol) for XIIId and then heated for 30 minutes with reflux. After cooling down, the resulting product is drawn off and cleaned by recrystallising from acetic acid.

In this way, for example, the 2,2-oxalato-1,3,2-dioxaborine XIIIa/1 is produced.

EXAMPLE 13

Synthesis of 4-methyl-1,3,2-dioxaborines XIV and XVI

A mixture of a (het)aromatic acetyl compound VII, VIIb, VIIc or VIId (0.1 mol) in acetic anhydride (0.6 mol) is treated using boron trifluoride-acetic acid-complex (0.2 mol) for VII and VIIb; (0.4 mol) for VIIc and (0.6 mol) for VIId and then heated for 3 hours to 45° C. After cooling down, the resulting product is drawn off and the raw product is cleaned by recrystallising from glacial acetic acid, but in some cases also chromatographically separated using silica gel with toluene/glacial acetic acid.

In this way, for example, the following 2,2-difluoro-1,3,2-dioxaborines XIV/XVI are produced.

| | | | | | |
|---|---|---|---|---|---|
| XIIIa/1 | [structure] | $\lambda_{max}$ 595 nm | $\lambda_F$ 650 nm | mp 338° C. | Yield 88% |

| | | | | | |
|---|---|---|---|---|---|
| XIV/1 | [structure] | λ_max 418 nm | λ_F 540 nm | mp 201° C. | Yield 45% |
| XVIa/1 | [structure] | λ_max 414 nm[b] | λ_F 483 nm[b] | mp 200° C. | Yield 33% |
| XVIb/1 | [structure] | λ_max 363 nm | λ_F 417 nm | mp 305° C. | Yield 88% |
| XVIc/1 | [structure] | λ_max 336 nm | λ_F 380 nm 409 nm 436 nm | mp 351° C. | Yield 49% |

EXAMPLE 14

Synthesis of Vinylogous 1,3,2-dioxaborines XV

A mixture from a 4-methyl-substituted 2,2-difluoro-1,3,2-dioxaborine XIV; or XVIa, XVIb or XVIc (0.001 mol) and the equivalent amount of a N,N-disubstituted 2-amino thiophene-5-carbaldahyde or an equal amount of an associate iminium salt in acetic anhydride (50 ml) is heated for 30 minutes in a water bath. It is then allowed to cool, which causes the crystals of the pigments to occur. These are drawn off and washed with ethyl acetate and ether.

In this way, for example, the following vinylogous 2,2-difluoro-1,3,2-dioxaborines XV are produced.

XVb/1 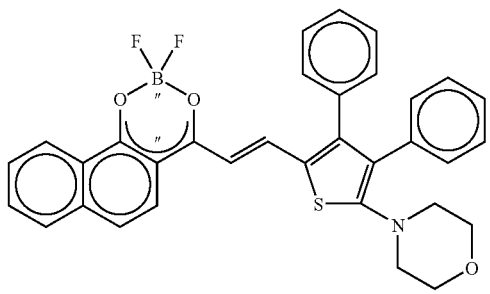
| $\lambda_{max}$ | $\lambda_F$ | mp | Yield |
|---|---|---|---|
| 604 nm | 642 nm | 171° C. | 90% |
XVb/2 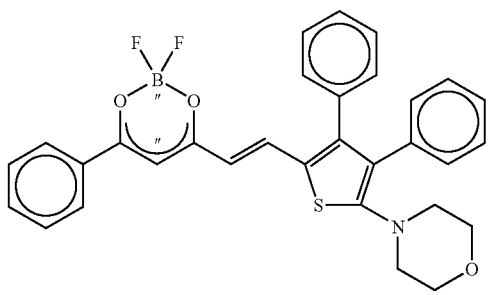
| $\lambda_{max}$ | $\lambda_F$ | mp | Yield |
|---|---|---|---|
| 565 nm | 642 nm | 168° C. | 35% |
XVb/3 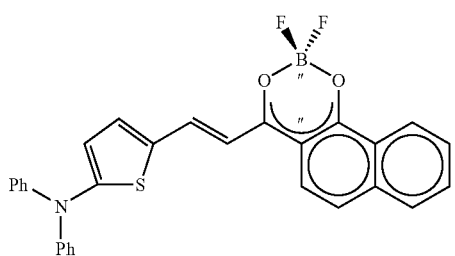
| $\lambda_{max}$ | $\lambda_F$ | mp | Yield |
|---|---|---|---|
| 604 nm | 670 nm | 287 | 75% |
XVc/1 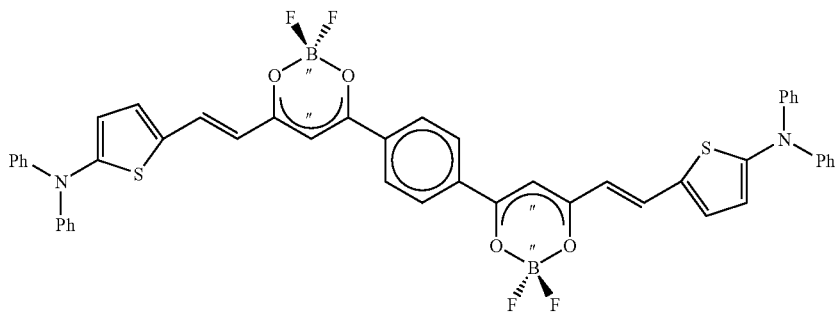
| $\lambda_{max}$ | $\lambda_F$ | mp | Yield |
|---|---|---|---|
| 648 nm | 758 nm | 319 | 85% |

-continued

XVd/1

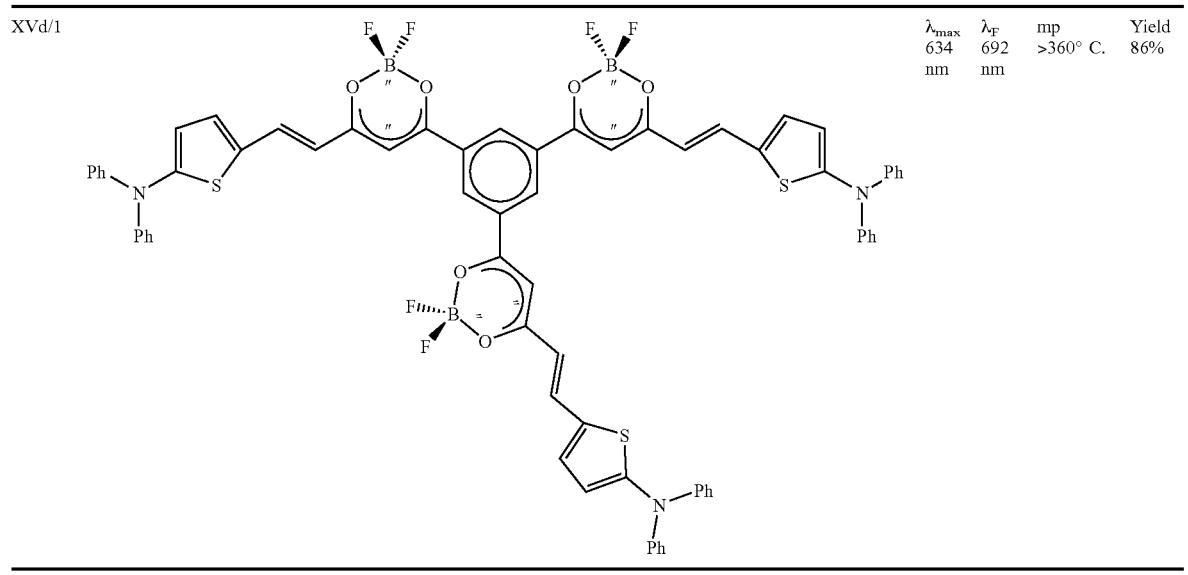

| | $\lambda_{max}$ | $\lambda_F$ | mp | Yield |
|---|---|---|---|---|
| | 634 nm | 692 nm | >360° C. | 86% |

To determine the spectroscopic data, the pigments were measured in the following solvents: without remark in $CH_2Cl_2$ a) in DMF
b) in $CHCl_3$
c) in acetone

EXAMPLE 15

Characteristics of an OLED With the Emitter Material XIa/1

The OLED was constructed by means of the following sequence of layers:

Anode: ITO (indium-tin oxide)
5 nm CuPc (Cu-Phthalocyanine)
55 nm 1-naphdata [4,4',4"-(1-naphthyl-phenyl amino)-triphenyl amine]
5 nm α NPD (N,N'di-1-naphthyl-N,N'dihenyl benzidine)
30 nm $Alq_3$+1.4% XIa/1
30 nm $Alq_3$ (aluminium-8-hydroxychinolate)
0.5 nm LiF (lithium fluoride)
Cathode 150 nm Al

What is claimed is:
1. A 1,3,2-dioxaborine luminophore of type XI, XII, XIII, XIV and/or XV having a formula selected from the group consisting of:

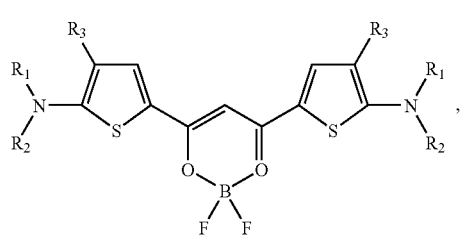

XIa

-continued

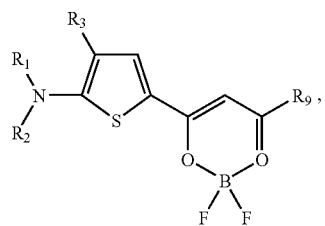

XIb

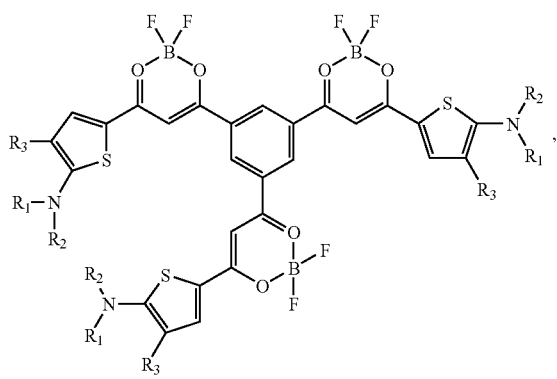

XIc

XId

-continued
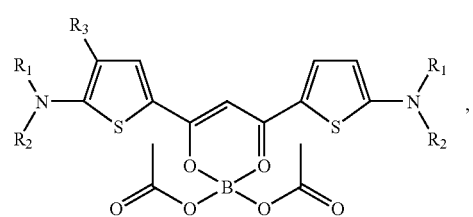
XIIa
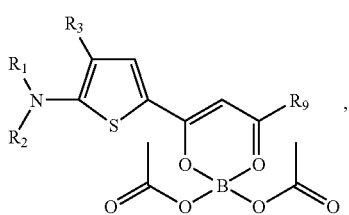
XIIb
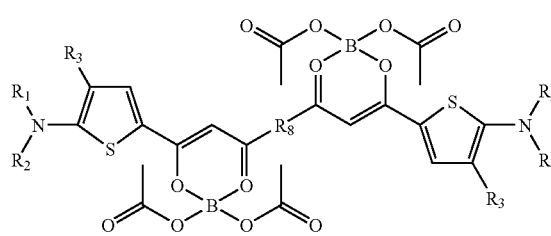
XIIc
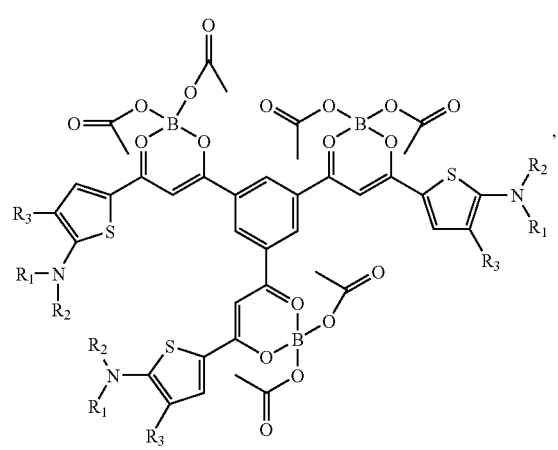
XIId
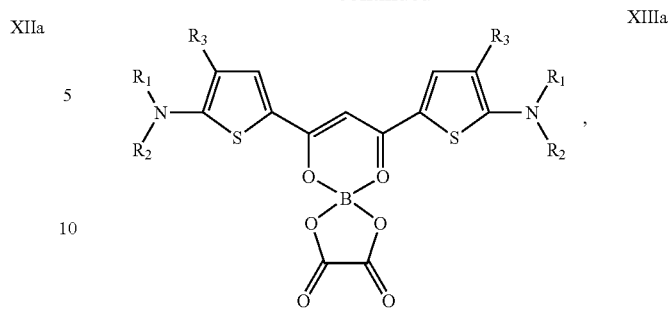
XIIIa
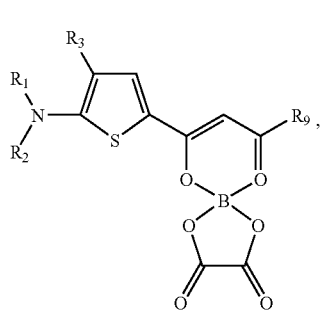
XIIIb
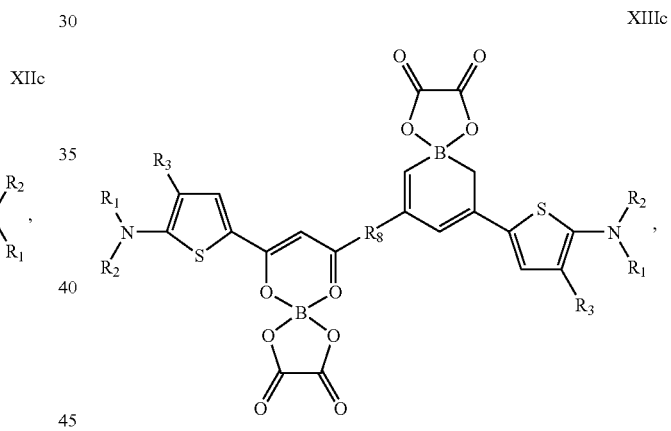
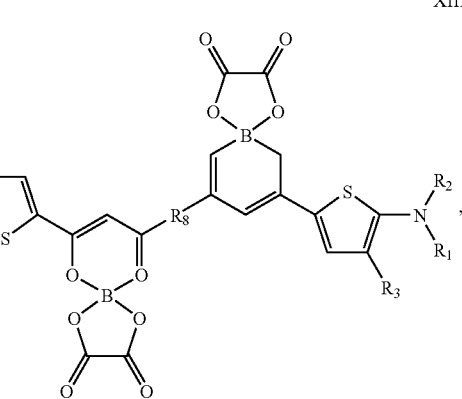
XIIIc
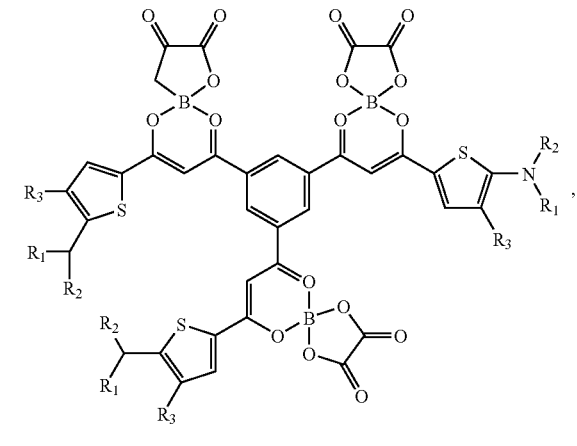
XIIId

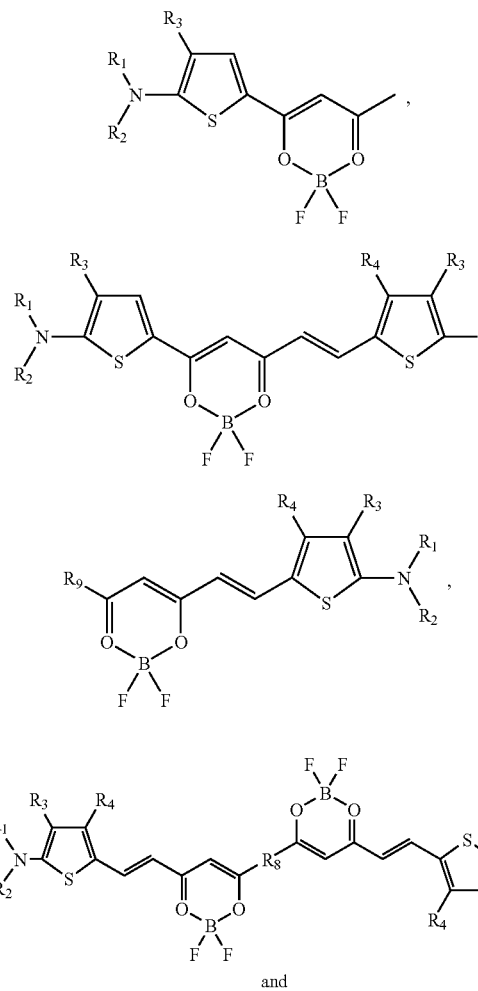

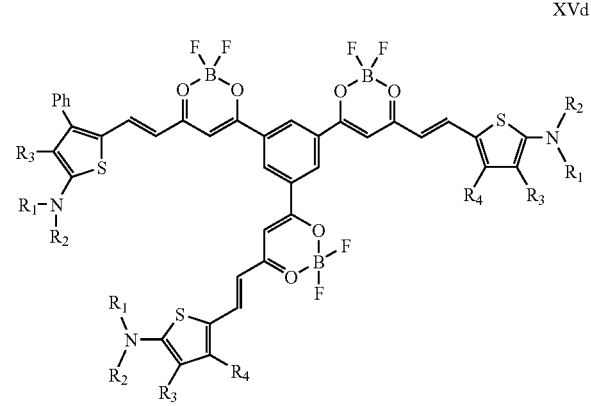

wherein:
- $R_1$, $R_2$, $R_3$, $R_4$ and $R_9$ are, independent of each other, a monofunctional (het) aryl system, that is a conjugated carboxylic and heterocyclic ring system that can also consist of linear or angular fused or combined ring types that are the same or different, whereby the peripheral hydrogen atoms may also be substituted by a alkyl, alkoxy, phenoxy, dialkylamino or diphenylamino groups;
- when said 1,3,2-dioxaborine luminophoreis is of the formula XV, XVb, XVc, or XVd, $R_1$ and $R_2$ may be branched or unbranched alkyl groupings or, together with the bonded N atom, can jointly form a pyrrolidine, piperidine or morpholine ring: $R_3$ and $R_4$ can also be H independent of each other;
- $R_8$ can be a chemical compound or a corresponding bi-functional (het) arylene system, that is a conjugated carboxylic or heterocyclic ring system that can also consist of linear or angular fused or combined ring types that are the same or different, whereby the peripheral hydrogen atoms can also be substituted by alkyl, alkoxy, phenoxy, dialkylamino or diphenylamino groups.

2. A method for the production of 1,3,2-dioxaborine luminophores having formulas selected from the groups consisting of:

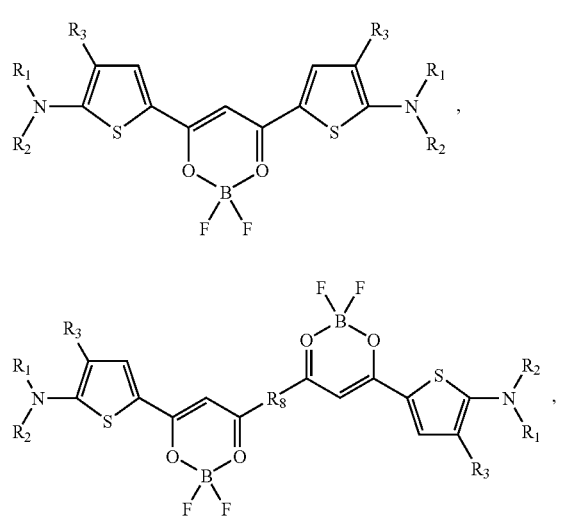

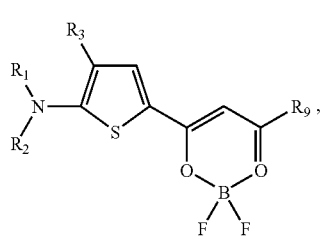

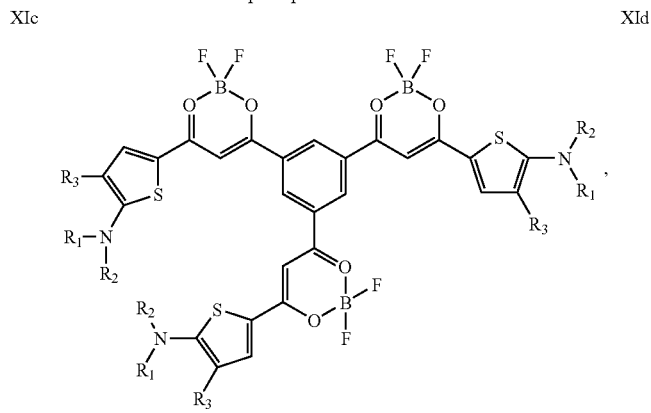

-continued

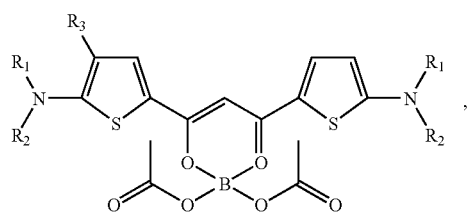 XIIa

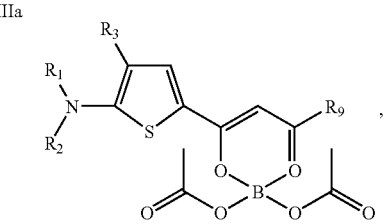 XIIb

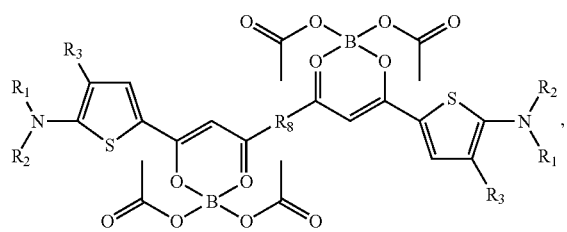 XIIc

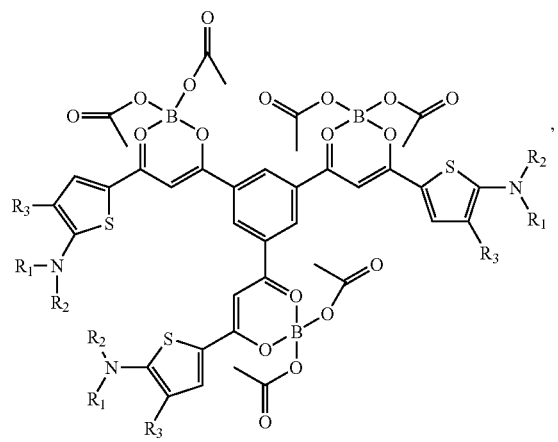 XIId

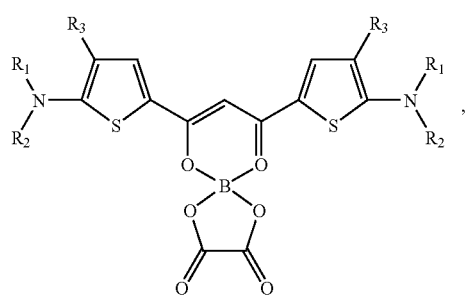 XIIIa

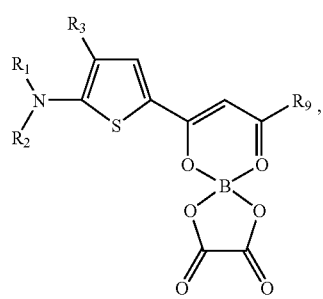 XIIIb

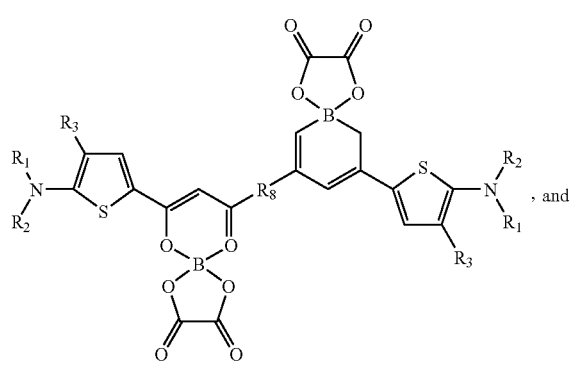 XIIIc

, and

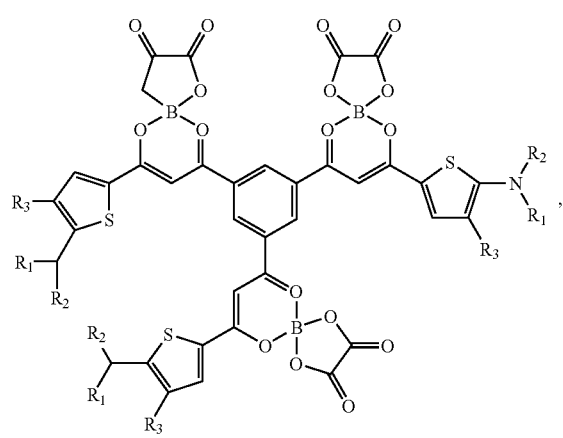 XIIId

, comprising:
converting 1,3-diketo derivates in acetic anhydride with a boric acid derivate.

3. A method according to claim 2, wherein two acetate ligands at a 1,3,2-dioxaborine luminophore are replaced by a bidentate ligand by means of a ligand exchange reaction.

4. A method according to claim 2, wherein an acetyl compound is, by means of the acylation reaction with boron trifluoride in acetic anhydride changed to the methylene-active 4-methyl-6-(het) aryl-2,2-difluoro-1,3,2-dioxaborine, and the vinylogous 1,3,2-dioxaborine luminophores having the formula XV, XVb, XVc, or XVd is obtained from the methylene-active compound with any aryl aldehyde in a following reaction stage.

5. A method according to claim 3, wherein an acetyl compound is, by means of the acylation reaction with boron trifluoride in acetic anhydride changed to the methylene-active 4-methyl-6-(het) aryl-2,2-difluoro-1,3,2-dioxaborine, and the vinylogous 1,3,2-dioxaborine luminophores having the formula XV, XVb, XVc, or XVd is obtained from the methylene-active compound with any aryl aldehyde in a following reaction stage.

6. A method according to claim 4, wherein the acetyl compound is a 2-N,N-disubstitued aminothiene-5-yl-acetophenone and/or the aryl aldehyde is a 2-N,N-disubstitued amino-5-formyl-thiophene.

7. A method of the emitting properties of an organic light emitting diode, comprising adding to said organic light emitting diode a 1,3,2-dioxaborine luminophore of types XI, XII, XIII, XIV and/or XV having a formula selected from the group consisting of:

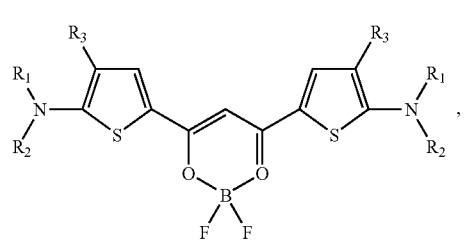
XIa

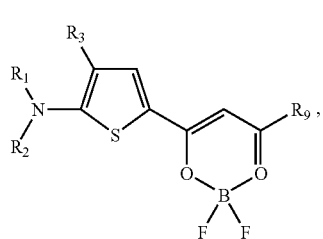
XIb

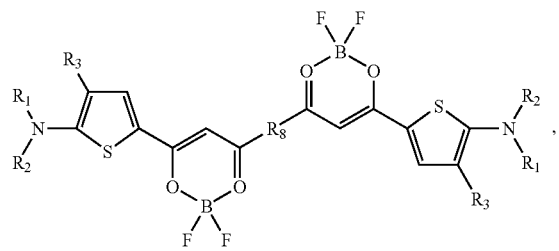
XIc

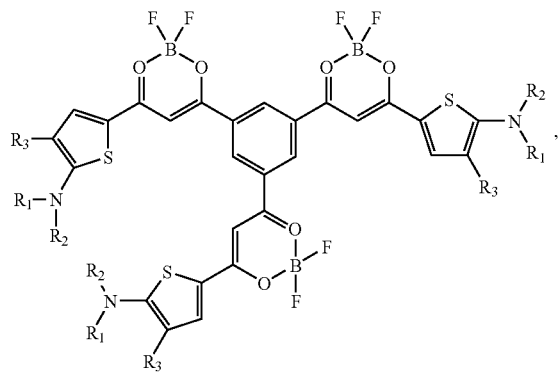
XId

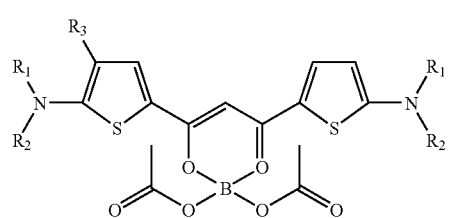
XIIa

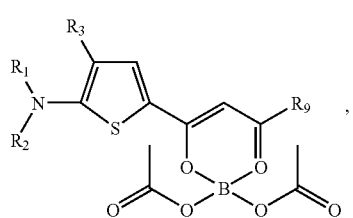
XIIb

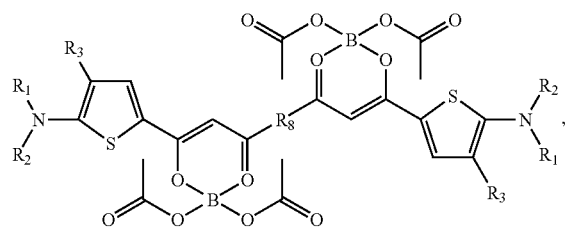
XIIc

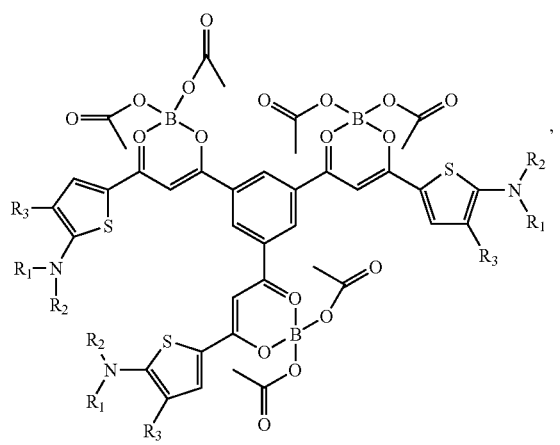
XIId

-continued
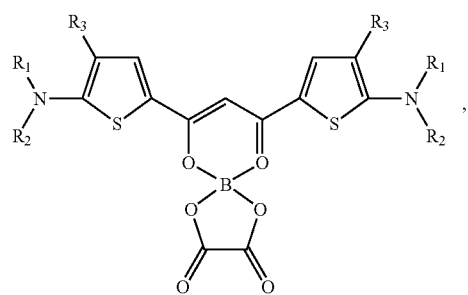
XIIIa
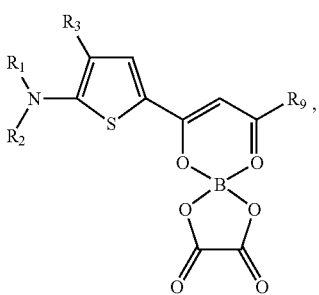
XIIIb
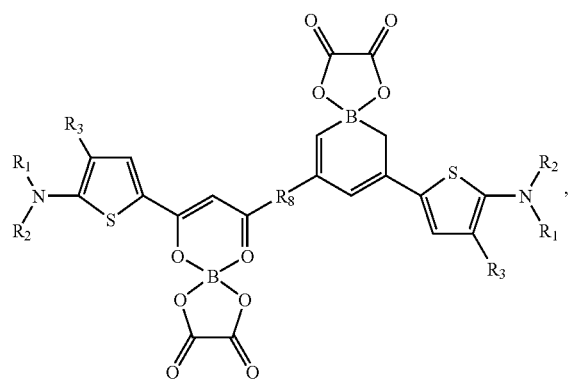
XIIIc
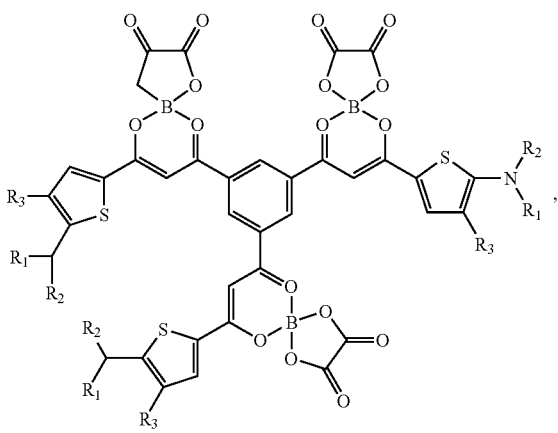
XIIId
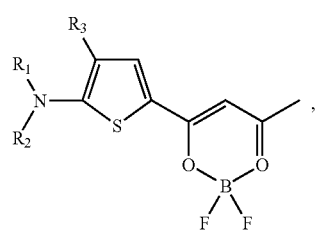
XIV
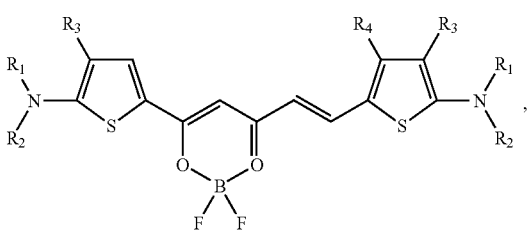
XV
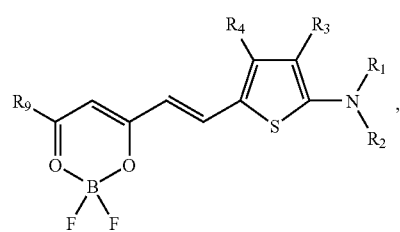
XVb
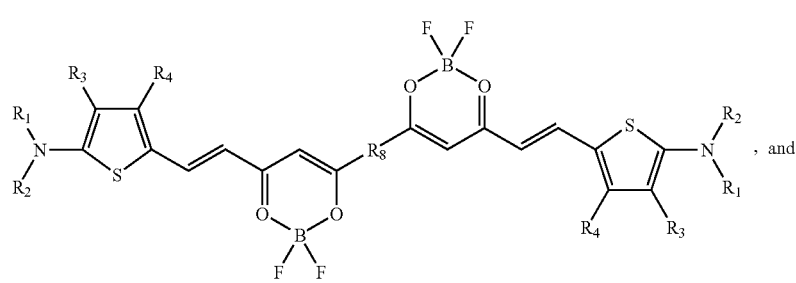
XVc
, and -continued
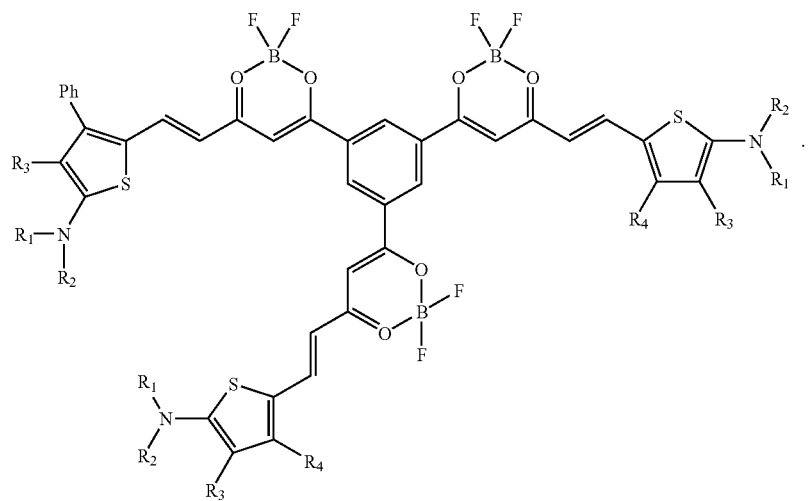
XVd
8. A method of enhancing the semi-conducting and/or emitting properties of an organic functional layer, comprising adding to said organic functional layer a 1,3,2-dioxaborine luminophore of types XI, XII, XIII, XIV and/or XV having a formula selected from the group consisting of:
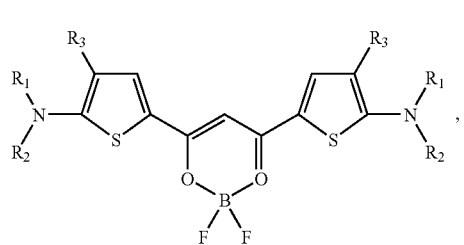
XIa
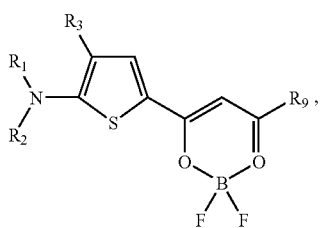
XIb
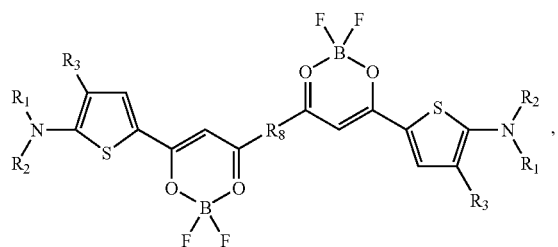
XIc
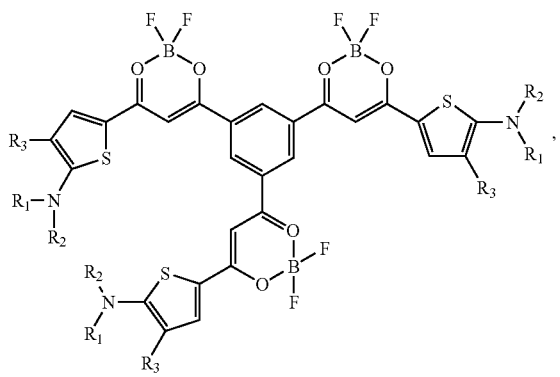
XId
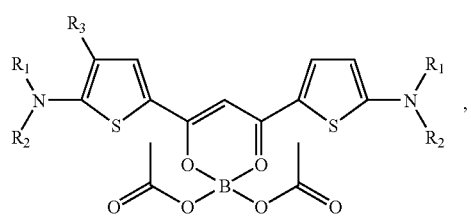
XIIa
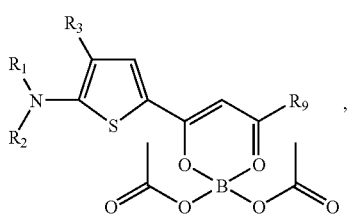
XIIb -continued
XIIc
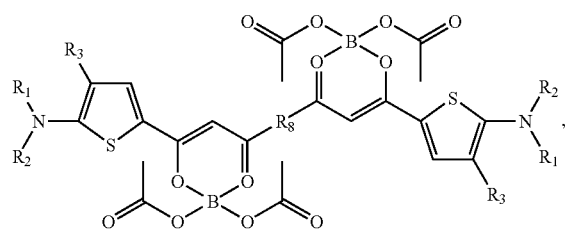
XIId
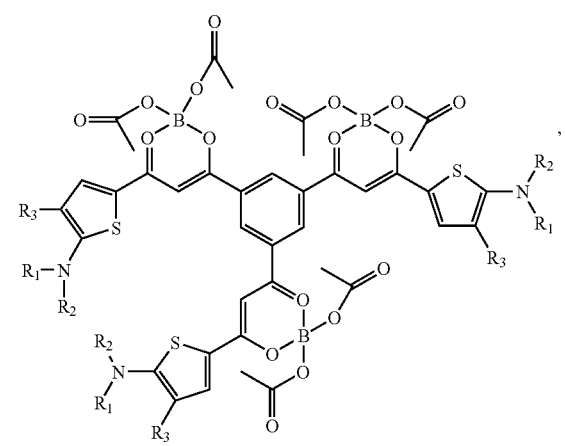
XIIIa
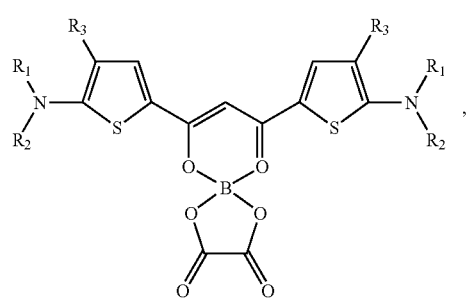
XIIIb
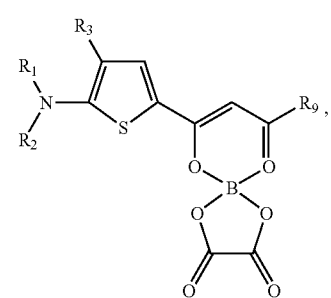
XIIIc
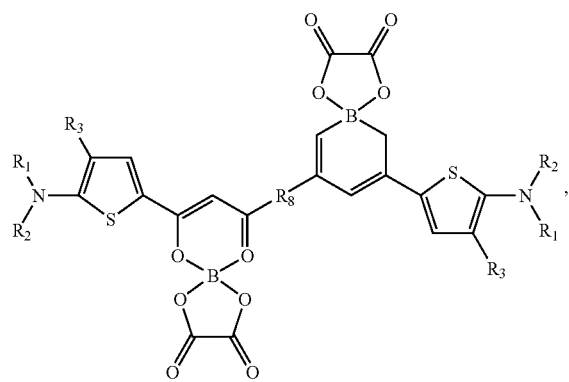
XIIId
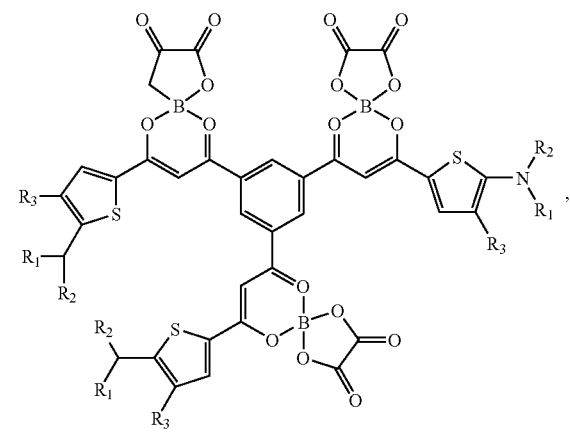
XIV
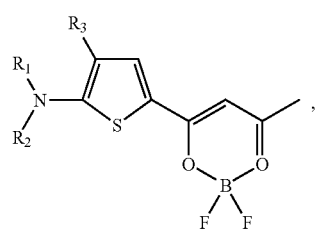
XV
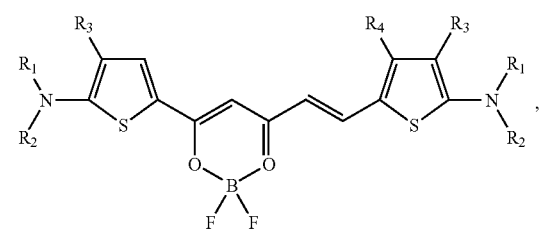
XVb
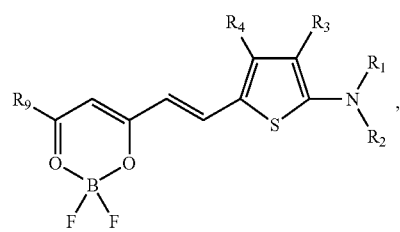

-continued
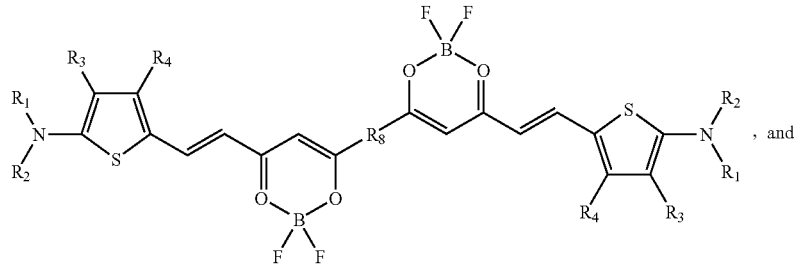
, and
XVc
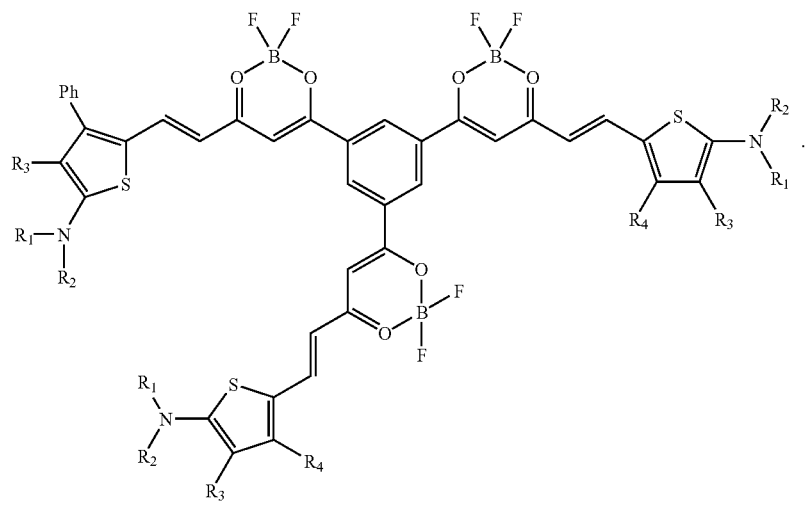
XVd
9. The method according to claim 8, wherein said organic functional layer is in a solar cell, in an organic field-effective transistor and/or a photo-refractive component.
* * * * *

UNITED STATES PATENT AND TRADEMARK OFFICE
CERTIFICATE OF CORRECTION

PATENT NO. : 7,026,490 B2
APPLICATION NO. : 10/467662
DATED : April 11, 2006
INVENTOR(S) : Horst Hartmann et al.

It is certified that error appears in the above-identified patent and that said Letters Patent is hereby corrected as shown below:

Claims 1, 2, 7 and 8 should appear as follows:

-- 1. A 1,3,2-dioxaborine luminophore of type XI, XII, XIII, XIV and/or XV having a formula selected from the group consisting of

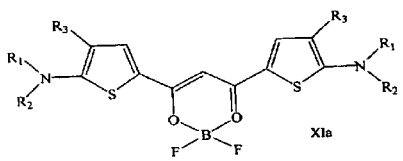
,

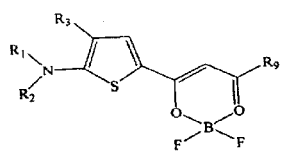
,

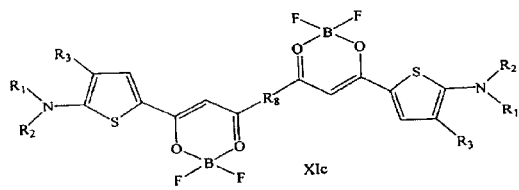
,

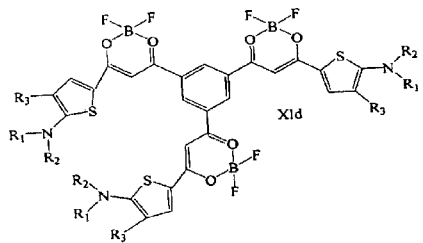
,

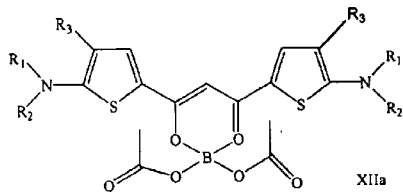
,

UNITED STATES PATENT AND TRADEMARK OFFICE
CERTIFICATE OF CORRECTION

PATENT NO. : 7,026,490 B2  Page 2 of 15
APPLICATION NO. : 10/467662
DATED : April 11, 2006
INVENTOR(S) : Horst Hartmann et al.

It is certified that error appears in the above-identified patent and that said Letters Patent is hereby corrected as shown below:

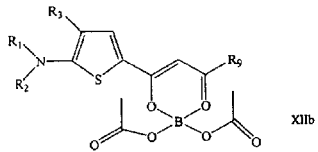

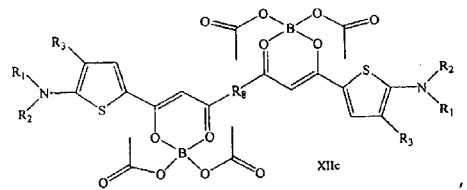

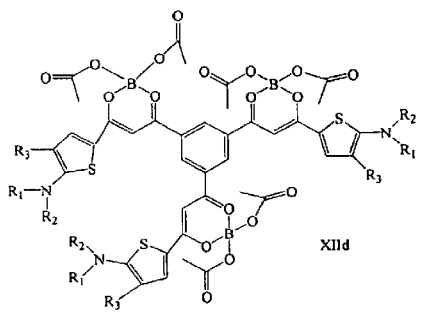

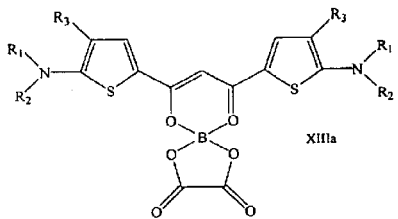

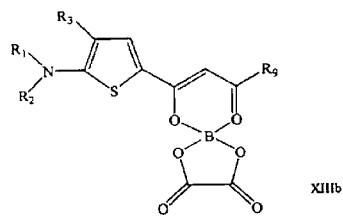

UNITED STATES PATENT AND TRADEMARK OFFICE
CERTIFICATE OF CORRECTION

| | | |
|---|---|---|
| PATENT NO. | : 7,026,490 B2 | Page 3 of 15 |
| APPLICATION NO. | : 10/467662 | |
| DATED | : April 11, 2006 | |
| INVENTOR(S) | : Horst Hartmann et al. | |

It is certified that error appears in the above-identified patent and that said Letters Patent is hereby corrected as shown below:

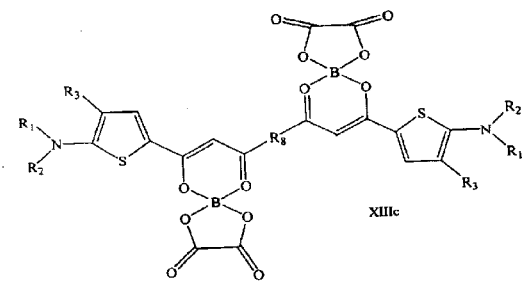

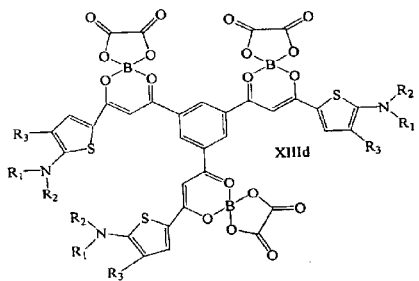

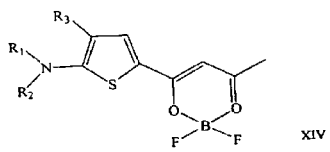

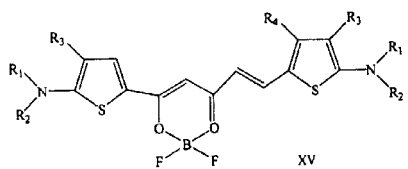

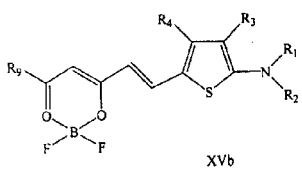

UNITED STATES PATENT AND TRADEMARK OFFICE
CERTIFICATE OF CORRECTION

PATENT NO. : 7,026,490 B2 Page 4 of 15
APPLICATION NO. : 10/467662
DATED : April 11, 2006
INVENTOR(S) : Horst Hartmann et al.

It is certified that error appears in the above-identified patent and that said Letters Patent is hereby corrected as shown below:

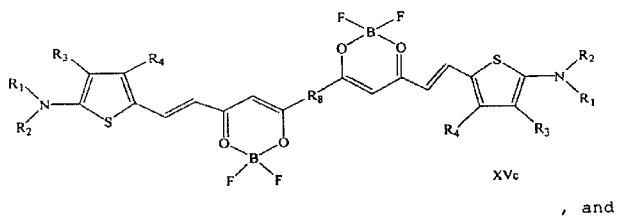

, and

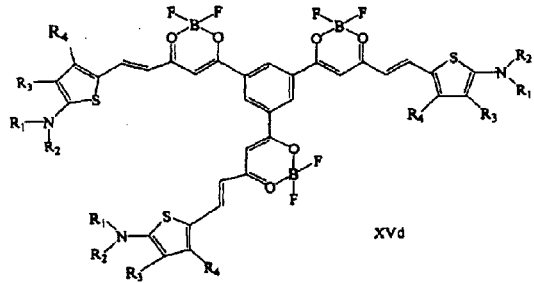

```
wherein:
R₁, R₂, R₃, R₄ and R₉ are, independent of each other, a
```
wherein:
$R_1$, $R_2$, $R_3$, $R_4$ and $R_9$ are, independent of each other, a monofunctional (het) aryl system, that is a conjugated carboxylic and heterocyclic ring system that can also consist of linear or angular fused or combined ring types that are the same or different, whereby the peripheral hydrogen atoms may also be substituted by a alkyl, alkoxy, phenoxy, dialkylamino or diphenylamino groups;

when said 1,3,2-dioxaborine luminophoreis is of the formula XV, XVb, XVc, or XVd, $R_1$ and $R_2$ may be branched or unbranched alkyl groupings or, together with the bonded N atom, can jointly form a pyrrolidine, piperidine or morpholine ring: $R_3$ and $R_4$ can also be H independent of each other;

$R_8$ can be a chemical compound or a corresponding bi-functional (het) arylene system, that is a conjugated carboxylic or heterocyclic ring system that can also consist of linear or angular fused or combined ring types that are the same or different, whereby the peripheral hydrogen atoms can also be substituted by alkyl, alkoxy, phenoxy, dialkylamino or diphenylamino groups.

UNITED STATES PATENT AND TRADEMARK OFFICE
CERTIFICATE OF CORRECTION

PATENT NO. : 7,026,490 B2
APPLICATION NO. : 10/467662
DATED : April 11, 2006
INVENTOR(S) : Horst Hartmann et al.

It is certified that error appears in the above-identified patent and that said Letters Patent is hereby corrected as shown below:

2. A method for the production of 1,3,2-dioxaborine luminophores having formulas selected from the groups consisting of,

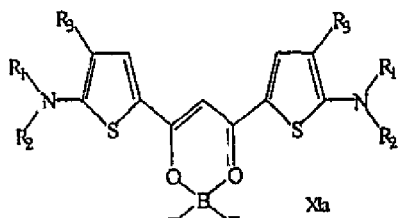

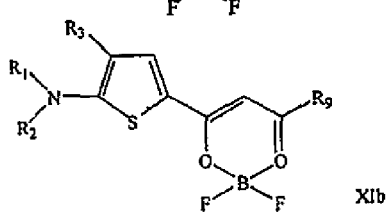

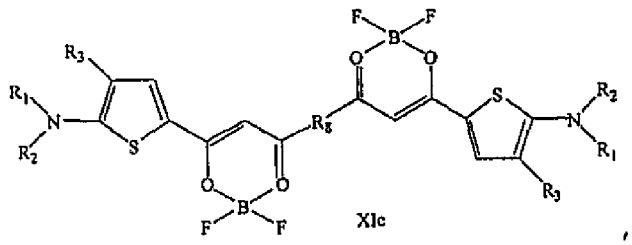

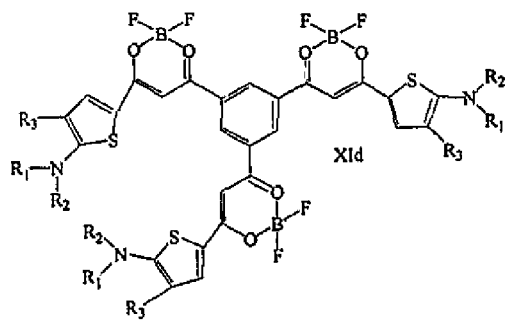

UNITED STATES PATENT AND TRADEMARK OFFICE
CERTIFICATE OF CORRECTION

PATENT NO. : 7,026,490 B2
APPLICATION NO. : 10/467662
DATED : April 11, 2006
INVENTOR(S) : Horst Hartmann et al.

It is certified that error appears in the above-identified patent and that said Letters Patent is hereby corrected as shown below:

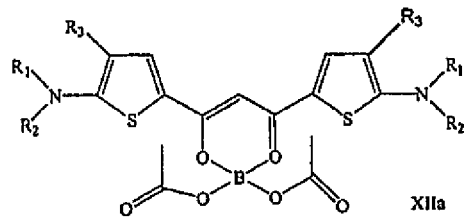
,

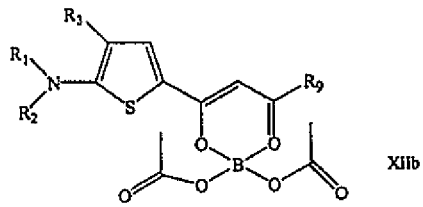
,

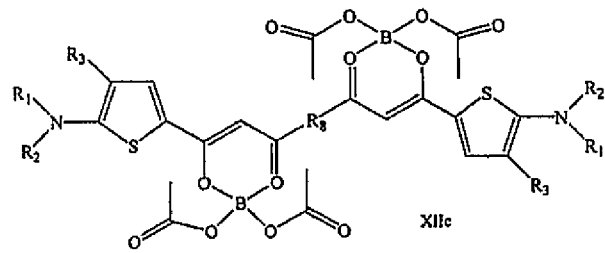
,

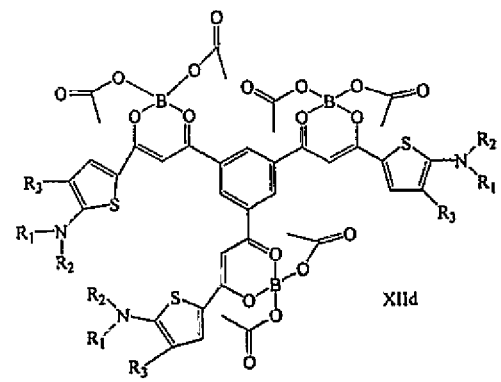
,

UNITED STATES PATENT AND TRADEMARK OFFICE
CERTIFICATE OF CORRECTION

PATENT NO.       : 7,026,490 B2
APPLICATION NO.  : 10/467662
DATED            : April 11, 2006
INVENTOR(S)      : Horst Hartmann et al.

It is certified that error appears in the above-identified patent and that said Letters Patent is hereby corrected as shown below:

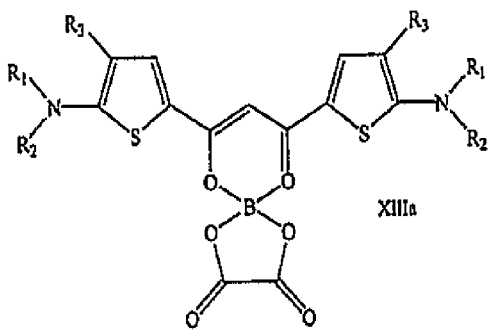

,

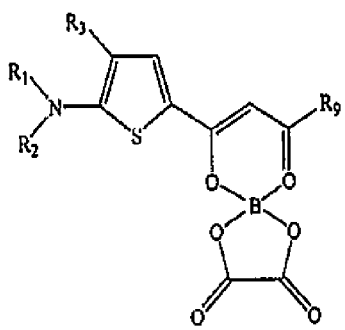

,

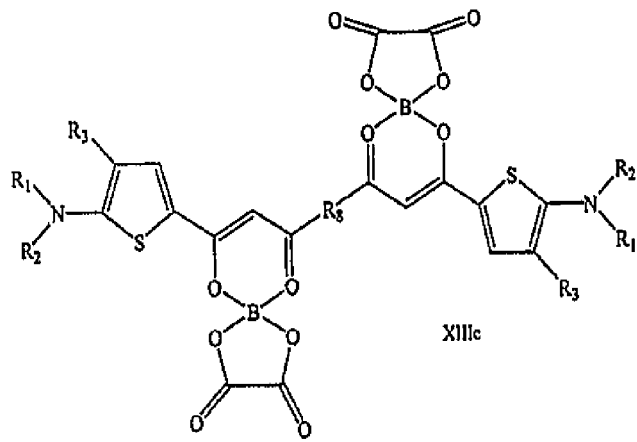

, and

UNITED STATES PATENT AND TRADEMARK OFFICE
CERTIFICATE OF CORRECTION

PATENT NO. : 7,026,490 B2
APPLICATION NO. : 10/467662
DATED : April 11, 2006
INVENTOR(S) : Horst Hartmann et al.

It is certified that error appears in the above-identified patent and that said Letters Patent is hereby corrected as shown below:

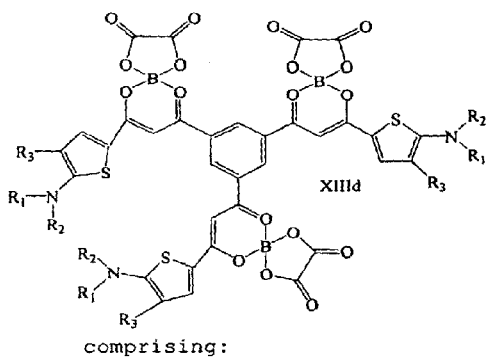

comprising:

converting 1,3-diketo derivates in acetic anhydride with a boric acid derivate.

7. A method of the emitting properties of an organic light emitting diode, comprising adding to said organic light emitting diode a 1,3,2-dioxaborine luminophore of types XI, XII, XIII, XIV and/or XV having a formula selected from the group consisting of

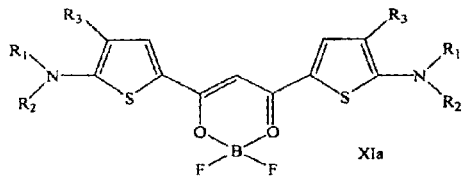

,

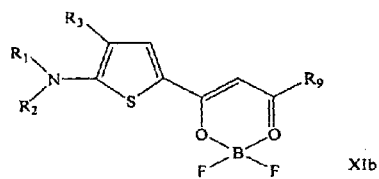

,

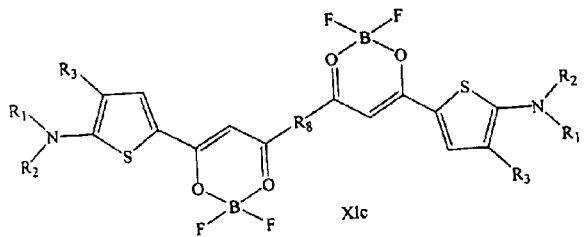

,

UNITED STATES PATENT AND TRADEMARK OFFICE
CERTIFICATE OF CORRECTION

PATENT NO. : 7,026,490 B2
APPLICATION NO. : 10/467662
DATED : April 11, 2006
INVENTOR(S) : Horst Hartmann et al.

It is certified that error appears in the above-identified patent and that said Letters Patent is hereby corrected as shown below:

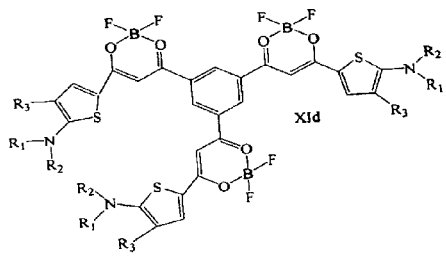

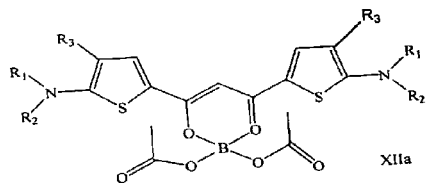

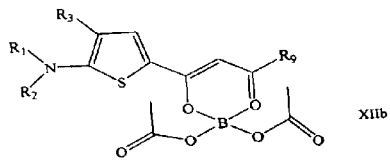

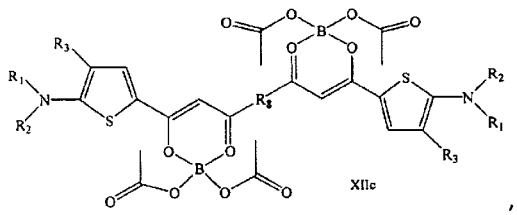

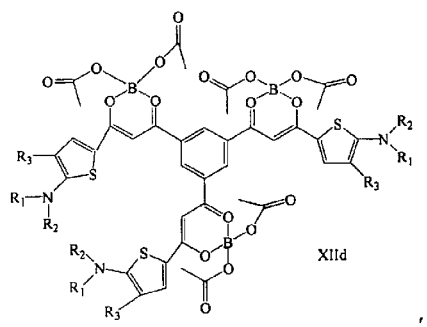

UNITED STATES PATENT AND TRADEMARK OFFICE
CERTIFICATE OF CORRECTION

PATENT NO. : 7,026,490 B2  
APPLICATION NO. : 10/467662  
DATED : April 11, 2006  
INVENTOR(S) : Horst Hartmann et al.

Page 10 of 15

It is certified that error appears in the above-identified patent and that said Letters Patent is hereby corrected as shown below:

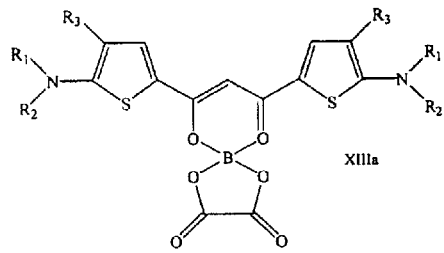

,

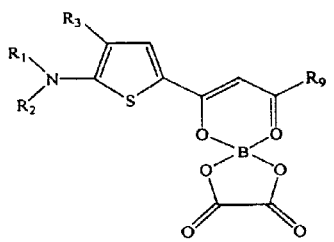

,

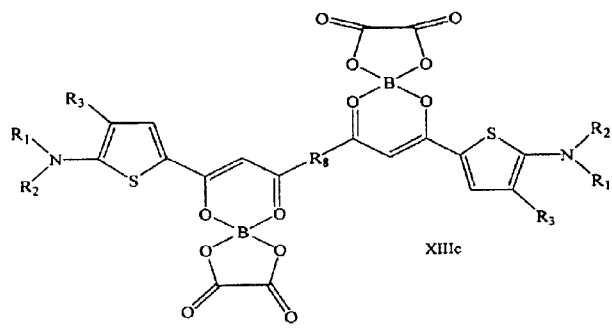

,

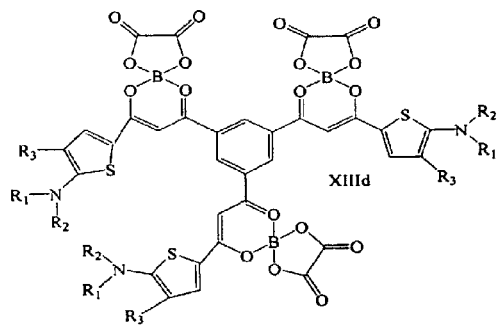

,

UNITED STATES PATENT AND TRADEMARK OFFICE
CERTIFICATE OF CORRECTION

PATENT NO. : 7,026,490 B2
APPLICATION NO. : 10/467662
DATED : April 11, 2006
INVENTOR(S) : Horst Hartmann et al.

It is certified that error appears in the above-identified patent and that said Letters Patent is hereby corrected as shown below:

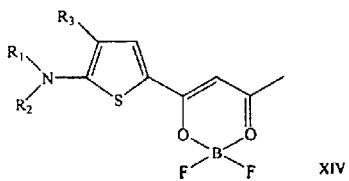
XIV ,

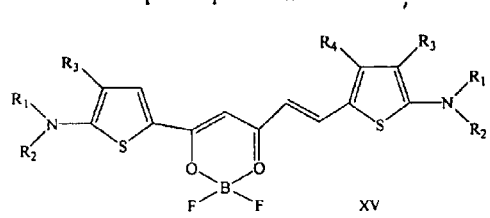
XV ,

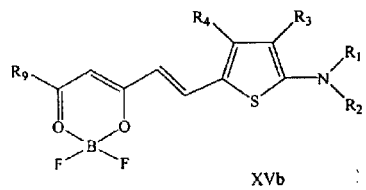
XVb ,

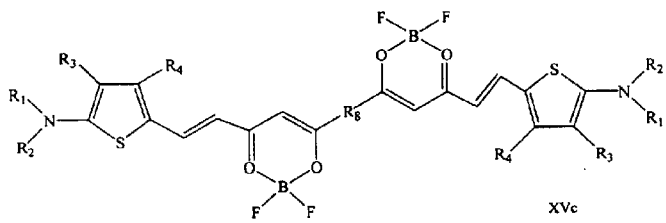
XVc
, and

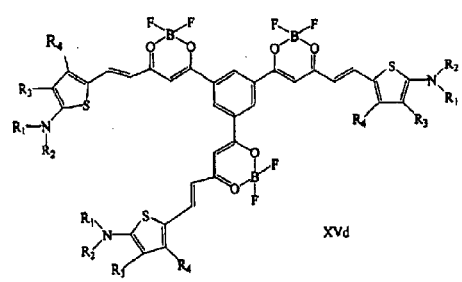
XVd

UNITED STATES PATENT AND TRADEMARK OFFICE
CERTIFICATE OF CORRECTION

PATENT NO.        : 7,026,490 B2
APPLICATION NO.   : 10/467662
DATED             : April 11, 2006
INVENTOR(S)       : Horst Hartmann et al.

It is certified that error appears in the above-identified patent and that said Letters Patent is hereby corrected as shown below:

```
8. A method of enhancing the semi-conducting and/or emitting
properties of an organic functional layer, comprising adding to
said organic functional layer a 1,3,2-dioxaborine luminophore of
types XI, XII, XIII, XIV and/or XV having a formula selected from
the group consisting of
```

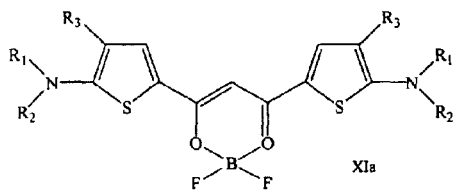

,

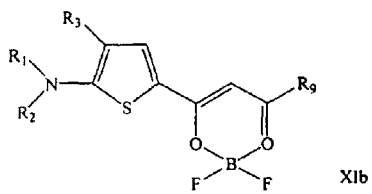

,

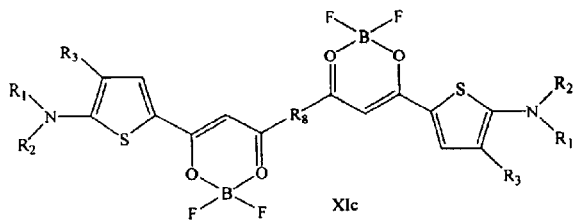

,

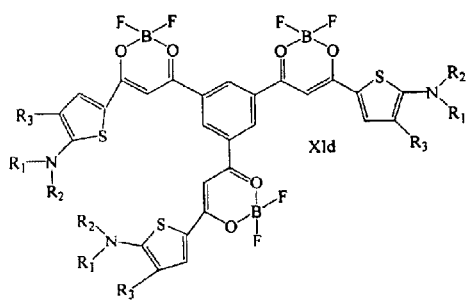

,

UNITED STATES PATENT AND TRADEMARK OFFICE
CERTIFICATE OF CORRECTION

PATENT NO. : 7,026,490 B2  Page 13 of 15
APPLICATION NO. : 10/467662
DATED : April 11, 2006
INVENTOR(S) : Horst Hartmann et al.

It is certified that error appears in the above-identified patent and that said Letters Patent is hereby corrected as shown below:

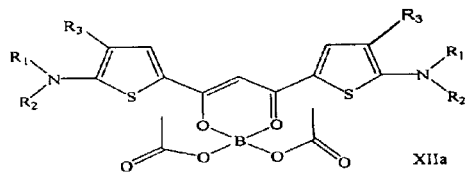

,

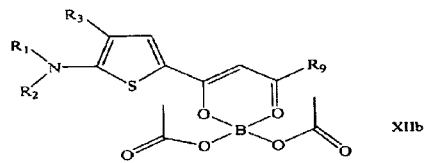

,

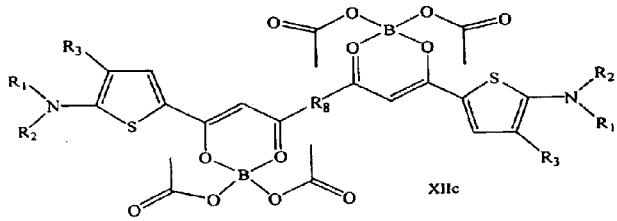

,

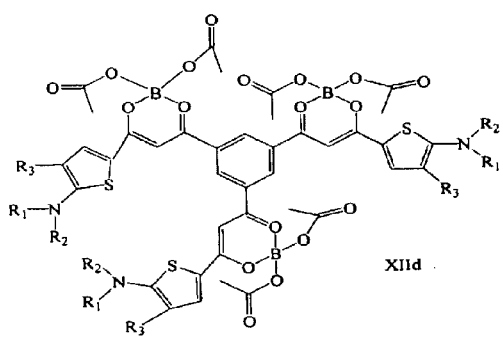

,

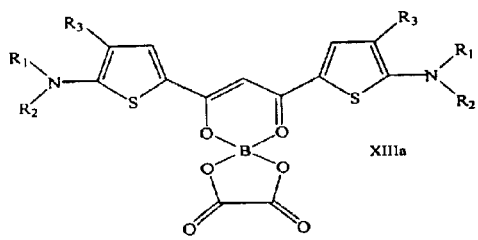

,

UNITED STATES PATENT AND TRADEMARK OFFICE
CERTIFICATE OF CORRECTION

PATENT NO. : 7,026,490 B2
APPLICATION NO. : 10/467662
DATED : April 11, 2006
INVENTOR(S) : Horst Hartmann et al.

It is certified that error appears in the above-identified patent and that said Letters Patent is hereby corrected as shown below:

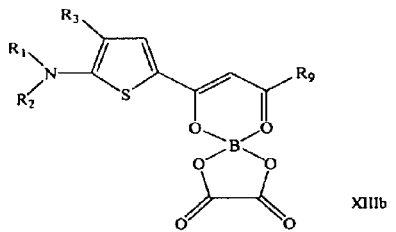

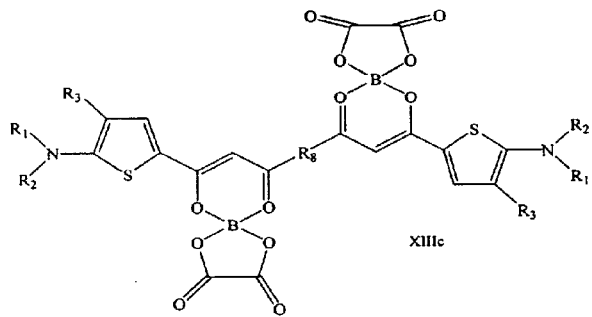

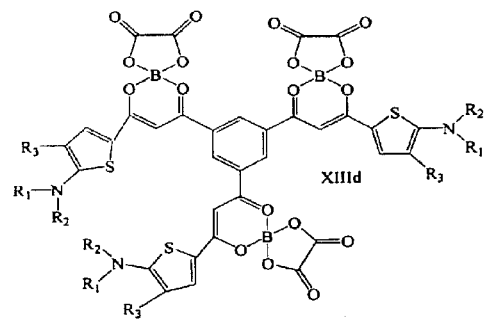

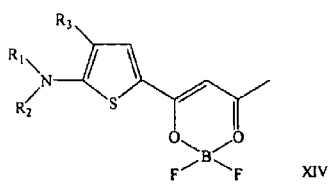

UNITED STATES PATENT AND TRADEMARK OFFICE
CERTIFICATE OF CORRECTION

PATENT NO. : 7,026,490 B2
APPLICATION NO. : 10/467662
DATED : April 11, 2006
INVENTOR(S) : Horst Hartmann et al.

It is certified that error appears in the above-identified patent and that said Letters Patent is hereby corrected as shown below:

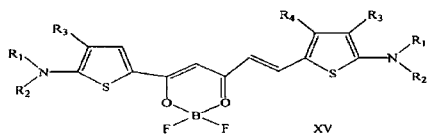

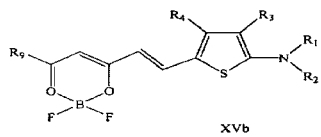

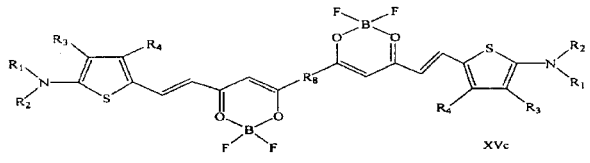

, and

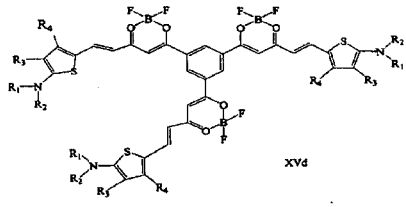

Signed and Sealed this

Twenty-eighth Day of November, 2006

JON W. DUDAS
*Director of the United States Patent and Trademark Office*